(12) United States Patent
Inoue

(10) Patent No.: US 6,558,396 B1
(45) Date of Patent: May 6, 2003

(54) APPARATUS FOR FOLDING INSTRUMENT AND USE OF THE SAME APPARATUS

(76) Inventor: Kanji Inoue, 98-13 , Miyazaki-cho, Shimogamo, Sakyo-ku, Kyoto-shi, Kyoto 606-0802 (JP)

( * ) Notice: Subject to any disclaimer, the term of this patent is extended or adjusted under 35 U.S.C. 154(b) by 0 days.

(21) Appl. No.: 09/720,871

(22) PCT Filed: May 6, 1999

(86) PCT No.: PCT/JP99/02386

§ 371 (c)(1),
(2), (4) Date: Jan. 2, 2001

(87) PCT Pub. No.: WO00/67674

PCT Pub. Date: Nov. 16, 2000

(51) Int. Cl.[7] ................................................ A61F 11/00
(52) U.S. Cl. ...................................... 606/108; 623/1.11
(58) Field of Search ........................... 606/108; 623/1.1, 623/1.11, 1.12, 1.23

(56) References Cited

U.S. PATENT DOCUMENTS

| | | | |
|---|---|---|---|
| 3,304,557 A | 2/1967 | Polansky | |
| 4,300,244 A | 11/1981 | Bokros | |
| 4,313,231 A | 2/1982 | Koyamada | |
| 4,338,934 A | 7/1982 | Spademan | |
| 4,502,159 A | * 3/1985 | Woodroof et al. | ............ 600/36 |
| 4,872,874 A | 10/1989 | Taheri | |
| 5,098,406 A | 3/1992 | Sawyer | |
| 5,104,399 A | 4/1992 | Lazarus | |

(List continued on next page.)

FOREIGN PATENT DOCUMENTS

| | | |
|---|---|---|
| DE | 4219949 | 12/1993 |
| EP | 0 464 755 A1 | 1/1992 |
| EP | 0472731 | 3/1992 |
| EP | 0786267 | 7/1997 |
| GB | 2164562 | 3/1986 |
| JP | 3-236836 | 10/1991 |
| JP | 4-25755 | 2/1992 |
| JP | 4-263852 | 9/1992 |
| JP | 5-212121 | 8/1993 |
| JP | 7-24072 | 1/1995 |
| JP | 3009638 | 2/1995 |
| JP | 6-63155 | 3/1995 |
| JP | 9-506524 | 6/1995 |
| JP | 9-511160 | 11/1997 |
| JP | 10-506292 | 6/1998 |
| WO | 91/12047 | 8/1991 |
| WO | 95/05788 | 2/1995 |
| WO | WO95/16406 | 6/1995 |
| WO | WO95/21592 | 8/1995 |
| WO | WO95/34255 | 12/1995 |
| WO | WO96/36387 | 11/1996 |

OTHER PUBLICATIONS

Kanji Inoue, et al., Aortic Arch Reconstruction by Transluminally Placed Endovascular Branched Stent Graft, Nov. 9, 1999, pp. II–316–321, vol. 100, No. 19, Circulation Supplement, Lippincott Williams & Wilkins.

*Primary Examiner*—Eduardo C. Robert
(74) *Attorney, Agent, or Firm*—Banner & Witcoff, Ltd.

(57) ABSTRACT

The device is to keep a collapsible/restorable elastic artificial blood vessel 1 in a collapsed condition, to transport the artificial blood vessel 1 to a target position and subsequently to restore the artificial blood vessel 1 into a predetermined shape by releasing it from the collapsed condition. The device comprises wrapping members 51, 52 which are generally flat when spread and wires 53, 54 which hold each of the wrapping members 51, 52 in a condition of being rolled, wherein each of a body portion 2 and a branch portion 3 of the artificial blood vessel 1 is contained inside the wrapping members 51, 52 held by the wires 53, 54 in a collapsed condition and the wires 53, 54 are separated from the wrapping members 51, 52 at the target position to spread the wrapping members 51, 52 so as to release the artificial blood vessel 1.

5 Claims, 18 Drawing Sheets

U.S. PATENT DOCUMENTS

| | | |
|---|---|---|
| 5,151,105 A | 9/1992 | Kwan-Gett |
| 5,183,085 A | 2/1993 | Timmermans |
| 5,199,948 A | 4/1993 | McPhee |
| 5,207,695 A | 5/1993 | Trout, III |
| 5,234,456 A | 8/1993 | Silvestrini |
| 5,236,447 A | 8/1993 | Kubo et al. |
| 5,242,452 A | 9/1993 | Inoue |
| 5,290,305 A | 3/1994 | Inoue |
| 5,330,528 A | 7/1994 | Lazim |
| 5,383,926 A | 1/1995 | Lock et al. |
| 5,387,235 A | 2/1995 | Chuter |
| 5,405,331 A | 4/1995 | Behnke et al. |
| 5,507,767 A | 4/1996 | Maeda et al. |
| 5,507,771 A | 4/1996 | Gianturco |
| 5,520,641 A | 5/1996 | Behnke et al. |
| 5,538,505 A | 7/1996 | Weinstein et al. |
| 5,554,181 A | 9/1996 | Das |
| 5,562,724 A | 10/1996 | Vowerk et al. |
| 5,569,205 A | 10/1996 | Hart et al. |
| 5,607,445 A | 3/1997 | Summers |
| 5,609,628 A | 3/1997 | Keranen |
| 5,628,783 A | 5/1997 | Quiachon et al. |
| 5,665,117 A | 9/1997 | Rhodes |
| 5,676,671 A | 10/1997 | Inoue |
| 5,693,089 A | 12/1997 | Inoue |
| 5,755,772 A | 5/1998 | Evans et al. |
| 5,755,773 A | 5/1998 | Evans et al. |
| 5,782,904 A | 7/1998 | White et al. |
| 5,824,037 A | 10/1998 | Fogarty et al. |
| 5,843,162 A | 12/1998 | Inoue |
| 5,873,880 A * | 2/1999 | Williams et al. ............ 128/898 |
| 5,925,076 A | 7/1999 | Inoue |
| 5,976,179 A | 11/1999 | Inoue |
| 6,013,100 A | 1/2000 | Inoue |
| 6,141,855 A * | 11/2000 | Morales ....................... 29/282 |
| 6,183,504 B1 | 2/2001 | Inoue |
| 6,245,097 B1 | 6/2001 | Inoue |
| 6,254,629 B1 | 7/2001 | Inoue |
| 6,254,630 B1 | 7/2001 | Inoue |
| 6,261,317 B1 | 7/2001 | Inoue |
| 6,270,520 B1 | 8/2001 | Inoue |
| 6,352,561 B1 * | 3/2002 | Leopold et al. ............ 623/1.11 |

* cited by examiner

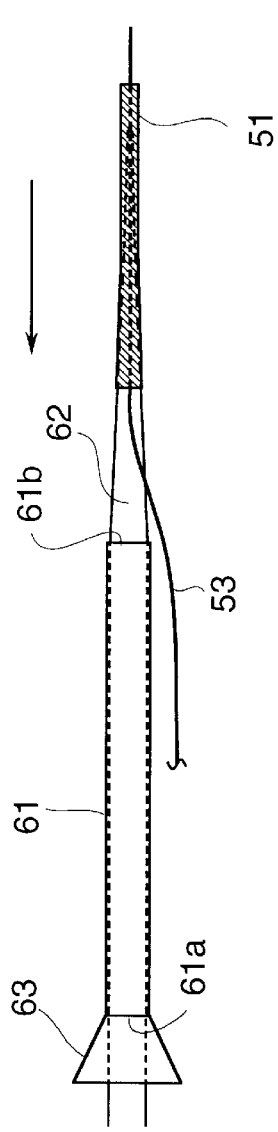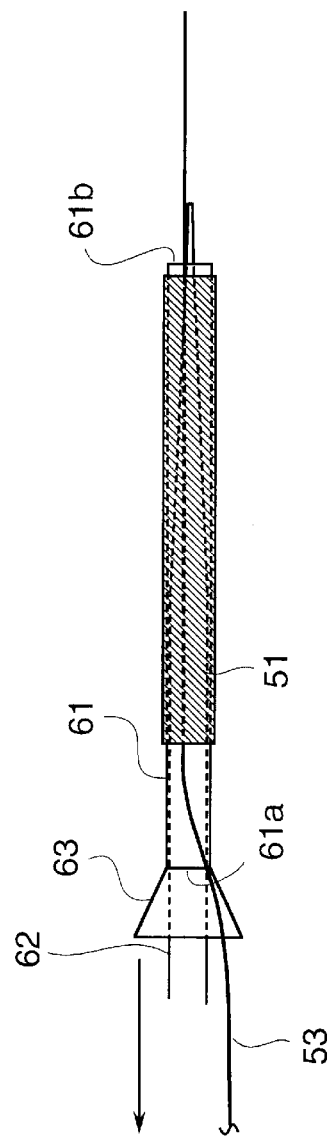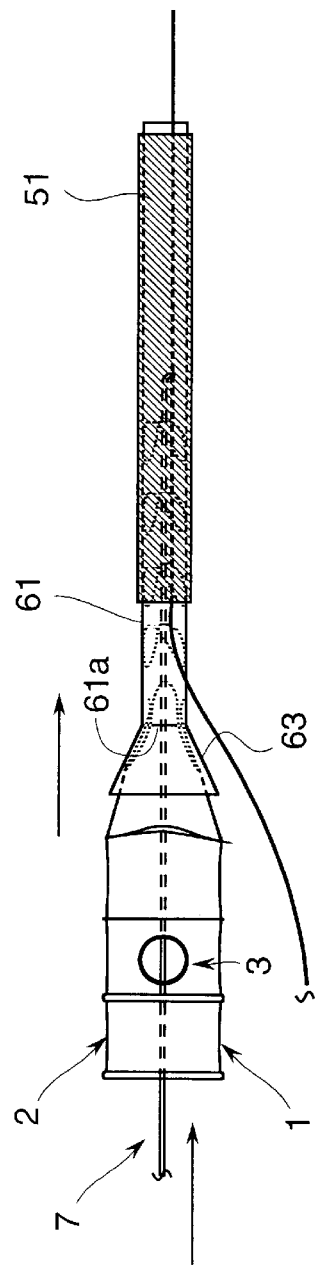

APPARATUS FOR FOLDING INSTRUMENT AND USE OF THE SAME APPARATUS

FIELD OF THE ART

This invention relates to a collapsing device for an appliance to be implanted which belongs to a field of medical devices and, more particularly, for artificial blood vessels or the like and a method of using the collapsing device.

BACKGROUND ART

With the recent progress of medical technique, a technique enabling transvascular use of a variety of appliances such as artificial blood vessel without ventrotomy has reached a clinical stage. Specific examples of such a technique include a method of transferring and fixing an artificial blood vessel using a catheter which has been invented by the inventor of present claimed invention and disclosed in the paper A.(for example, PCT/JP96/01347 which has been published with International Publication No. WO96/36387). This method includes; inserting a catheter into a human body through an inguinal artery to position a front end thereof near an affected portion in which an aneurysm or the like is present, inserting a tubular artificial blood vessel provided with collapsible/restorable elasticity into the catheter in a collapsed condition, transporting the artificial blood vessel to a predetermined location near the affected portion by the use of a transporting device or a hauling device, and releasing the artificial blood vessel from the catheter at the location, thereby to position the artificial blood vessel in an affected blood vessel having the aneurysm.

In the above-described document a collapsing device for keeping the artificial blood vessel in a collapsed condition during transportation works as follows; the artificial blood vessel is bound by a string at given portions of an outer circumference thereof, a retaining rod is passed into the string to keep the artificial blood vessel in a collapsed condition so as to release the collapsed condition from a remote place, the artificial blood vessel is transported to a target position and subsequently the retaining rod is drawn out of the string to release the string so as to restore the artificial blood vessel.

However, in order to make it possible to transport the artificial blood vessel smoothly, it is preferable to collapse the artificial blood vessel in a more appropriate condition. For example, in the artificial blood vessel described in the above document collapsible/restorable ring members are arranged intermittently along an axial direction. Due to this arrangement of the ring member, a protuberance is made locally on an outer face of the artificial blood vessel when the artificial blood vessel is collapsed by means of a string. Consequently, a dragging resistance will be generated while transporting the artificial blood vessel in a catheter. As a result, in order to reduce the dragging resistance, it is more preferable to make protuberances generate as least as possible on the outer face of the collapsed artificial blood vessel.

DISCLOSURE OF THE INVENTION

In order to solve the above problems a collapsing device for an appliance in accordance with the invention comprises a wrapping member which is generally flat when spread and a retaining member which holds the wrapping member in a condition of being rolled in order to keep a collapsible/restorable elastic appliance in a collapsed condition, to transport the appliance to a target position and subsequently to restore the appliance into a predetermined shape by releasing it from the collapsed condition, and is characterized by that the appliance is contained inside the wrapping member which is held by the retaining member in a collapsed condition and then the retaining member is separated from the wrapping member at the target position to spread the wrapping member so as to release the appliance.

It is effective if the wrapping member is made of an expansible material. For further improve a stretching properties it is effective if the wrapping member is in a shape of a mesh, and especially it is preferable that the mesh is woven with wefts and warps or the wrapping member is made of polyurethane fibers.

As a concrete embodiment to facilitate holding or spreading the wrapping member, it is represented that the retaining member is a wire rod which sews overwrapped edges of the wrapping member. As a concrete example of the wire rod it is preferable to use a wire made of nickel titanium. The wire rod may be a string which sews the overwrapped edges of the wrapping member and so arranged that a retaining member is passed through a loop formed at an end portion of the string.

As a preferable example to which the present claimed invention is applied it is represented that the appliance is in a shape of a tube and so arranged as to be contained inside the wrapping member held by the retaining member in a collapsed condition. Among the above, it can be a more preferable example to which the present claimed invention is applied that the appliance is so arranged that intermittently arranged ring members are bridged by a flexible cover and each of the ring members is collapsed into a wavy shape having a peak and a valley alternately and repeatedly along a circumferential direction thereof.

As another preferable example to which the present claimed invention is applied, it is represented that the appliance comprises a tubular body portion and a tubular branch portion which branches from a part of the tubular body portion with its internal space communicating with the body portion and so arranged that the body portion of the appliance is contained in a first wrapping member held by a first retaining member in a collapsed condition and the branch portion is contained in a second wrapping member held by a second retaining member in a collapsed condition. Among the above, it can be a more preferable example that the appliance is so arranged that the body portion is so made that intermittently arranged ring members are bridged by a flexible cover and the branch portion is so made that intermittently arranged ring members are bridged by a flexible cover with its internal space communicating with a part of the body portion, wherein the body portion and the branch portion of the appliance are so arranged that each of the ring members is folded into a wavy shape having a peak and a valley alternately and repeatedly along a circumferential direction thereof.

As a simple method of using the collapsing device in accordance with the present claimed invention, it is preferable that the wrapping member is mounted on near an end portion of an outer circumference of a pipe member, the appliance is inserted into inside of the pipe member at a position corresponding to the position where the wrapping member is mounted and the wrapping member and the appliance are simultaneously drawn out of the pipe member in a condition that both of the wrapping member and the appliance are restrained from moving interactively at the end portion so as to contain the appliance inside of the wrapping member.

If the appliance has a branch, the following step is preferable; the first wrapping member is mounted on near an end portion of an outer circumference of a pipe member, the body portion and the branch portion of the appliance are inserted together into inside of the pipe member at a position corresponding to the position where the first wrapping member is mounted, the first wrapping member and the body portion are drawn simultaneously out of the pipe member in a condition that both of the first wrapping member and the body portion are restrained from moving interactively at the end portion so as to contain the body portion and the branch portion of the appliance together inside of the first wrapping member, subsequently a part of the first wrapping member is released from a condition of being held by the first retaining member, the branch portion is drawn out through the part of the first wrapping member, then the second wrapping member is mounted on near an end portion of an outer circumference of a pipe member, the branch portion is inserted into inside of the pipe member at a position corresponding to the position where the second wrapping member is mounted and the second wrapping member and the branch portion are drawn simultaneously out of the pipe member in a condition that both of the second wrapping member and the branch portion are restrained from moving interactively at the end portion so as to contain the branch portion inside of the second wrapping member.

In order to make it easier to mount the wrapping member it is preferable that the wrapping member is made to open wider gradually along a tapered guide portion and then to be mounted on an outer circumference of the pipe member arranged at a position continuous to the guide portion. It is preferable that the guide portion is applied with a material of cutting frictional resistance such as silicon or the like.

As a procedure after transporting the collapsing device in accordance with the present claimed invention the following procedure is effective; the appliance is transported to a target position, the appliance is restored into a predetermined shape by releasing the wrapping member from a condition of being held by the retaining member and then the retaining member is removed from the target position with the wrapping member left at the position together with the appliance.

In accordance with the collapsing device of the invention, since whole of the appliance is contained inside of the tubular wrapping member, it is possible to reduce a protuberance which is generated locally on an outer face of the appliance compared with a case in which the appliance is bound with a string partially to keep a collapsed condition. In addition, if the appliance is released from a condition of being held by the retaining member at a target position, the wrapping member is spread and a space surrounding the collapsed appliance will be open wide. As a result, interference with a movement of restoring the appliance into a predetermined shape can effectively be avoided.

In this case, if the wrapping member is made of an expansible material, the material of the wrapping member stretches so as to wrap the appliance effectively when the wrapping member is held to wrap the appliance whereas the material of the wrapping member shrinks so as to be quickly separated from the appliance and move to a certain position near the target position when the wrapping member is released from a condition of being held.

In case the material of the wrapping member is in a shape of a mesh, a stretching properties can effectively be demonstrated because a cross of the mesh stretches or shrinks.

If the mesh is woven with wefts and warps, a stretching properties can sufficiently be demonstrated along both of lengthwise and crosswise and a cross of the mesh is hard to be moved as well as hard to be loosened, thereby to produce the above-mentioned effects for certain.

If the material of the wrapping member is made of polyurethane fibers, it is easy to provide the material with a stretching properties, in addition, the wrapping material can be left at a target portion in a body together with the appliance after released because polyurethane fibers are not harmless to a human body.

If the retaining member is a wire rod and overwrapped edges of the wrapping member are sewed by the wire rod, it is possible not only to keep the wrapping member in a shape of a tube but also to release the wrapping member directly from a condition of being held with relatively little resistance by pulling the wire rod lengthwise.

If the wire rod is made of a wire of nickel titanium, it is possible to obtain an extremely flexible elasticity, thereby to be convenient for transporting the appliance. In addition, a length of the wrapping member can be adjusted depending on a demand since it is possible to cut only the wrapping member along a direction at right angles generally to the wire in a condition of passing the wire therethrough without cutting the wire, if necessary. Further, if the above-mentioned wire is used, there is no fear of getting entangled like a thread.

With an arrangement in which the retaining member is a string which sews edges of the wrapping member and a retaining rod is passed through a loop formed at an end portion of the string, it is possible not only to hold the wrapping member in a shape of a tube but also to release the wrapping member from a condition of being held indirectly if the string is released from restraint of moving by hauling the retaining member so as to draw the retaining member out of the loop. If a string having elasticity is used, it is easy to release the string out of the loop, thereby to be especially effective.

In accordance with the invention, it is extremely effective in collapsing a tubular appliance like an artificial blood vessel which becomes bulky when restored into a predetermined shape. More specifically, if the appliance is so arranged that ring members arranged intermittently are bridged by a flexible cover and each of the ring members is collapsed into a wavy shape having a peak and a valley alternately and repeatedly along a circumferential direction thereof, it is likely to happen that protuberance is made locally on the outer face of the appliance due to collapsed ring members. However, since whole of the appliance in accordance with the invention is wrapped by the wrapping member including protuberance, it is possible to firmly press down protuberance, thereby to form a smooth curved surface on the outer face thereof.

In addition, in accordance with the invention, for a branched appliance wherein a tubular branched portion branches from a tubular body portion it is possible to collapse the branched appliance like an appliance in a tubular shape as a whole by applying a wrapping member and a retaining member to each of the body portion and the branch portion respectively. In case each of the body portion and the branch portion is so made that intermittently arranged ring members are bridged by a cover, it is possible to firmly press down protuberance generated on the body portion or the branch portion, thereby to form a smooth curved surface, on the outer face of the body portion and the branch portion respectively.

Since the method of using the collapsing device of the invention comprises steps of mounting the wrapping member on near an end portion of an outer circumference of a pipe member, inserting the appliance into inside of the pipe member and drawing the wrapping member and the appliance simultaneously out of the pipe member in a condition that both of the wrapping member and the appliance are restrained from moving interactively at the end portion, it is possible to contain the appliance inside of the wrapping member in an appropriate collapsed condition through simple procedures, even though the wrapping member is highly elastic and the appliance is highly elastically restorable.

For a branched appliance, if a procedure comprises steps of collapsing the body portion by the use of the first wrapping member and the first retaining member, releasing a part of the first wrapping member from a condition of being held by the first retaining member, drawing the branch portion out of the first wrapping member through the part and collapsing the branch portion by the use of the second wrapping member and second retaining member, it is possible to keep the body portion and the branch portion in an appropriate collapsed condition respectively without causing a big inconvenience in spite of the branched appliance.

If the wrapping member is mounted on an outer circumference of the pipe member along a tapered guide portion to open wider gradually, it is possible to move the wrapping member to the outer circumference of the pipe member so as to be mounted thereon with ease and securely even if a shrinkage degree of the wrapping member is so high that the wrapping member shrinks quite a lot.

If the appliance is transported to a target position, and restored into a predetermined shape by releasing the wrapping member from a condition of being held by the retaining member and subsequently only the retaining member is released from the target position with the wrapping member left at the position together, it is not necessary to remove the wrapping member, thereby to simplify a procedure of transporting the appliance.

BRIEF DESCRIPTION OF THE DRAWINGS

FIG. 5 is a view for explaining a procedure to collapse the artificial blood vessel with the collapsing device.

FIG. 6 is a view for explaining the procedure to collapse the artificial blood vessel with the collapsing device.

FIG. 7 is a view for explaining the procedure to collapse the artificial blood vessel with the collapsing device.

BEST MODES OF EMBODYING THE INVENTION

The invention will be described in detail with reference to the embodiments thereof shown in the accompanying drawings.

Figure 1:
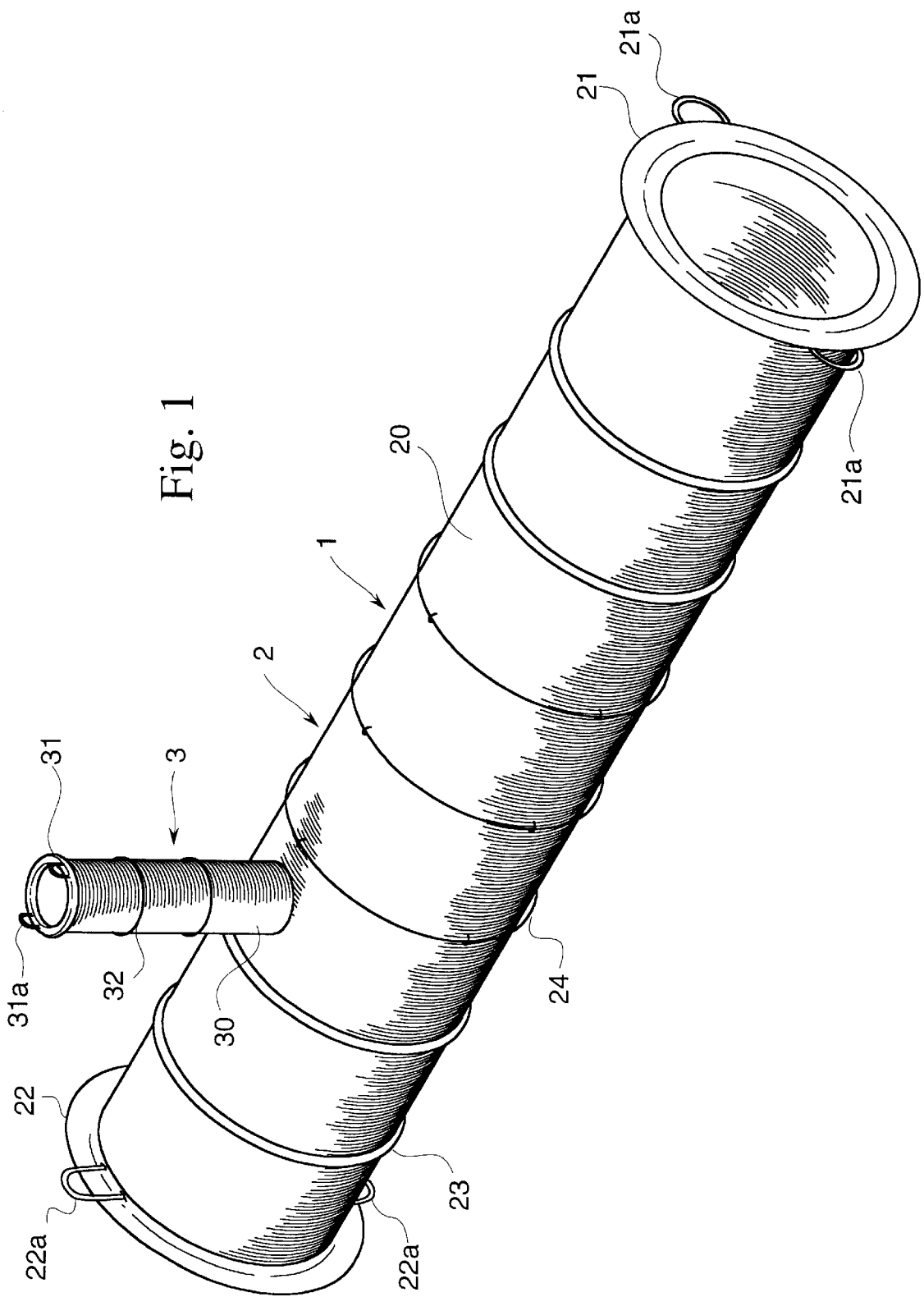
FIG. 1 is a perspective view of a branched artificial blood vessel to which one embodiment of the invention is applied.

FIG. 1 shows a branched artificial blood vessel 1 as an appliance to which a collapsing device of the embodiment is applied in a condition before it is collapsed. A fundamental arrangement of the artificial blood vessel 1 is described in documents such as the above-described document A (PCT/JP96/01347 (International Laid Open Number WO96/36387)) which has been disclosed by the inventor of this invention. A fundamental arrangement of this embodiment will now be described according to the document A. A body portion 2 of the artificial blood vessel 1 has a structure comprising end ring members 21, 22 having collapsible/restorable elasticity and intermediate ring members 23, 24 having collapsible/restorable elasticity interposed between the end ring members 21 and 22. A branch portion 3 of the artificial blood vessel 1 has a structure comprising an end ring member 31 and an intermediate ring member 32 interposed between the end ring member 31 and the body portion 2. The ring members 21, 22, 23, 24 are bridged by a flexible, tensile and waterproof tubular cover 20 and the ring members 31, 32 are bridged by a flexible, tensile and waterproof tubular cover 30 so as to form the branched artificial blood vessel 1. Internal spaces of the tubular covers 20 and 30 are liquidtightly connected at a connecting portion.

Figure 16:
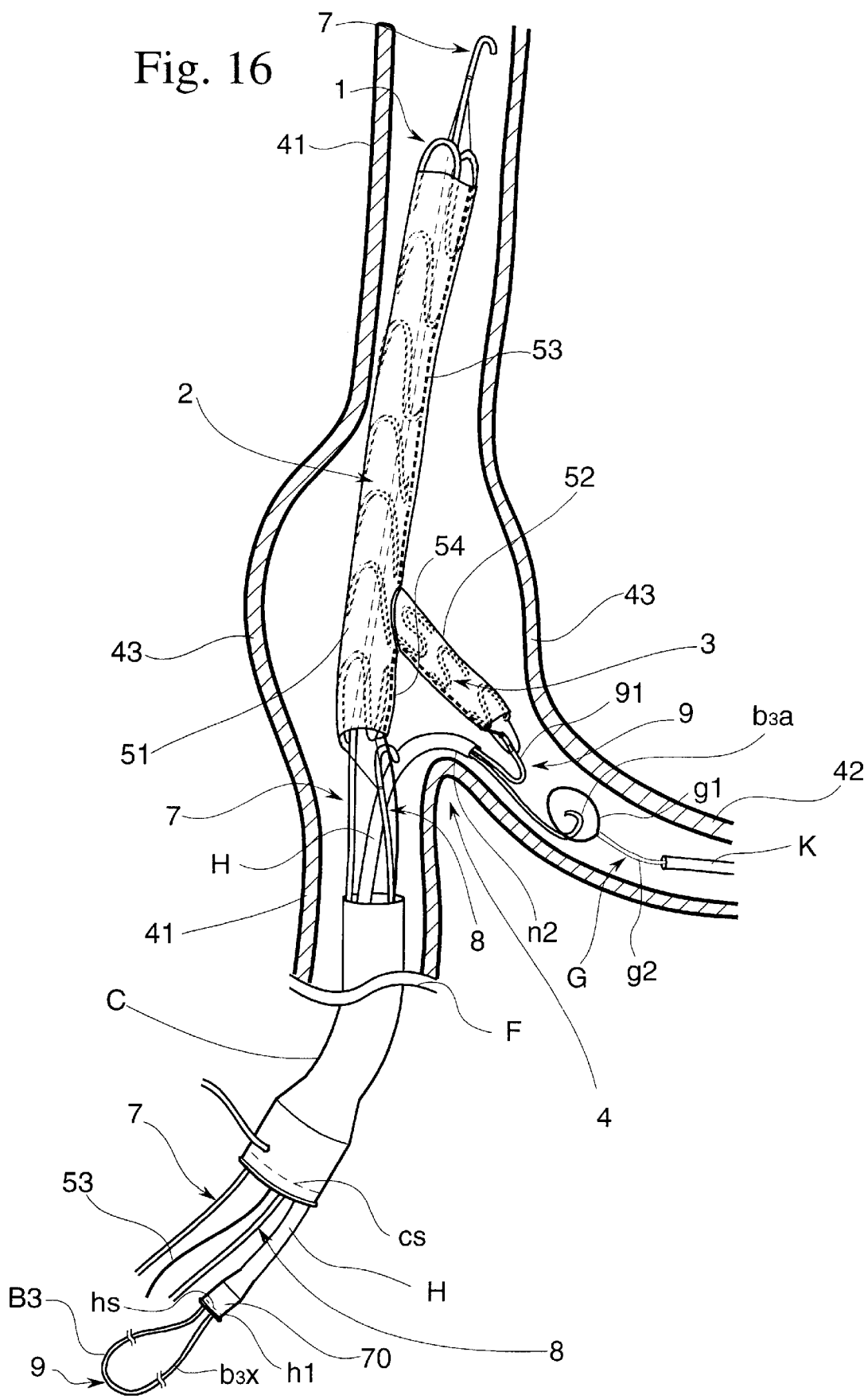
FIG. 16 is a view for explaining a procedure to implant the artificial blood vessel of the embodiment into a target position.

FIG. 16 schematically shows the artificial blood vessel 1 and a bifurcated portion 4 where a bifurcated blood vessel 42 bifurcated from a trunk blood vessel 41 at which the artificial blood vessel 1 is to be implanted. The trunk blood vessel 41 is, for example, an arcuate artery and the bifurcated blood vessel 42 is an artery which locates at a peripheral side of the trunk blood vessel 41. The branched artificial blood vessel 1 is introduced to be implanted into an aneurysm 43 at the bifurcated portion 4 to prevent blood flowing into the aneurysm 43.

For introducing the artificial blood vessel 1 a transvessel procedure is adopted; the artificial blood vessel 1 is kept in a collapsed condition, inserted into a groin F of the thigh through a sheath C, transported to a target position and then restored into a predetermined shape by releasing a condition of being kept. For this transvessel procedure the artificial blood vessel 1 is collapsed into a small size by a collapsing device 5 shown in FIG. 2.

The collapsing device 5 comprises a first and a second wrapping members 51 and 52, and a first and a second wires 53 and 54 as a first and a second retaining members.

Figure 3:
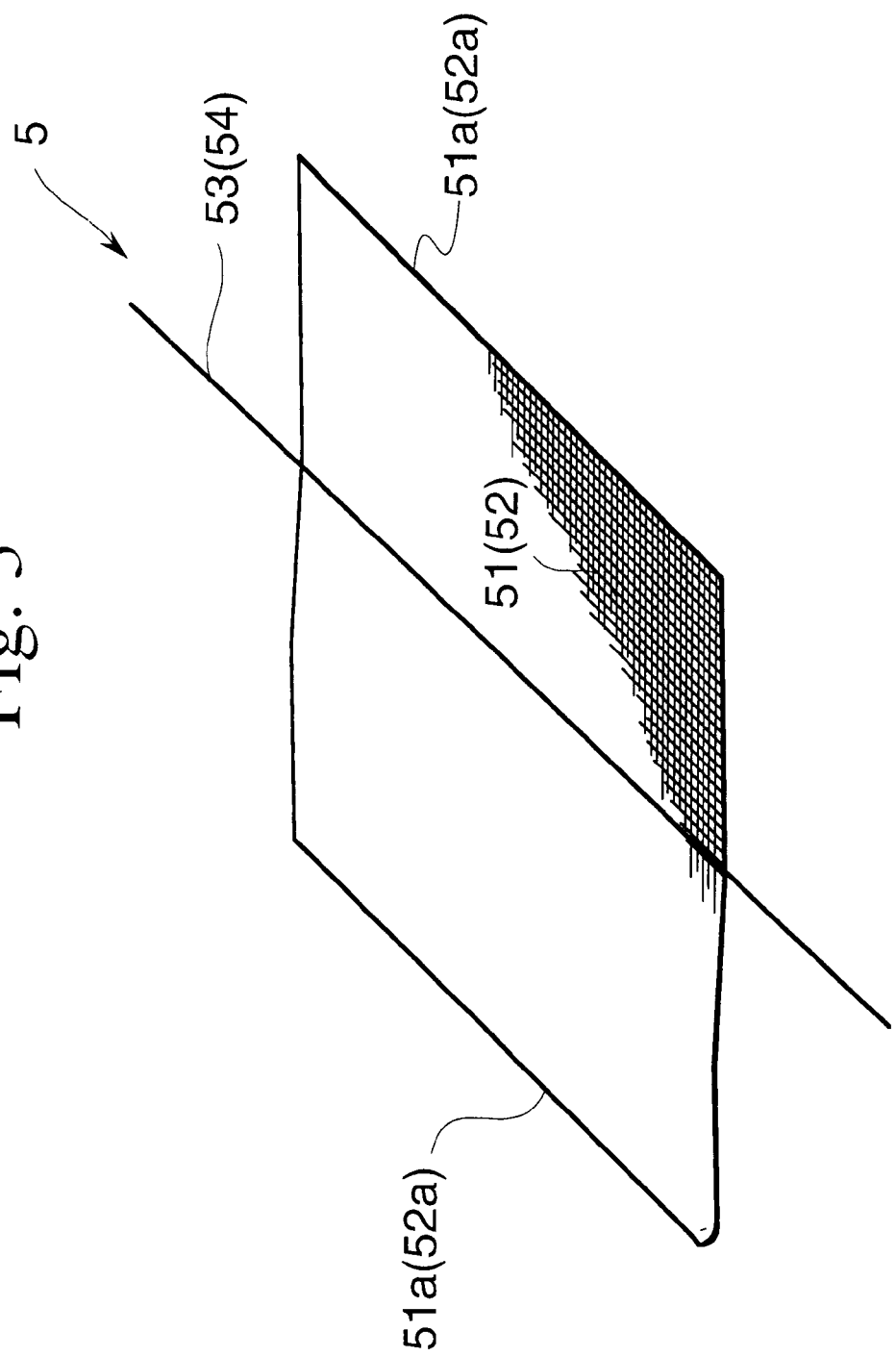
FIG. 3 is a perspective view of the collapsing device in a condition of being spread.

The first wrapping member 51 is to wrap the body portion 2 of the artificial blood vessel 1, and interwoven with wefts and warps of polyurethane fibers (generally called spandex fibers) to form a mesh as shown in FIG. 3 so as to be expansible and generally flat when spread. The wefts and warps are interwoven at each points of intersection and stretching of a cross of the mesh formed at the intersection provides whole of the first wrapping member 51 with stretching properties along lengthwise and crosswise directions. The second wrapping member 52 is to wrap the branch portion 3 of the artificial blood vessel 1 and has the same arrangement as that of the first wrapping member 51.

Figure 4:
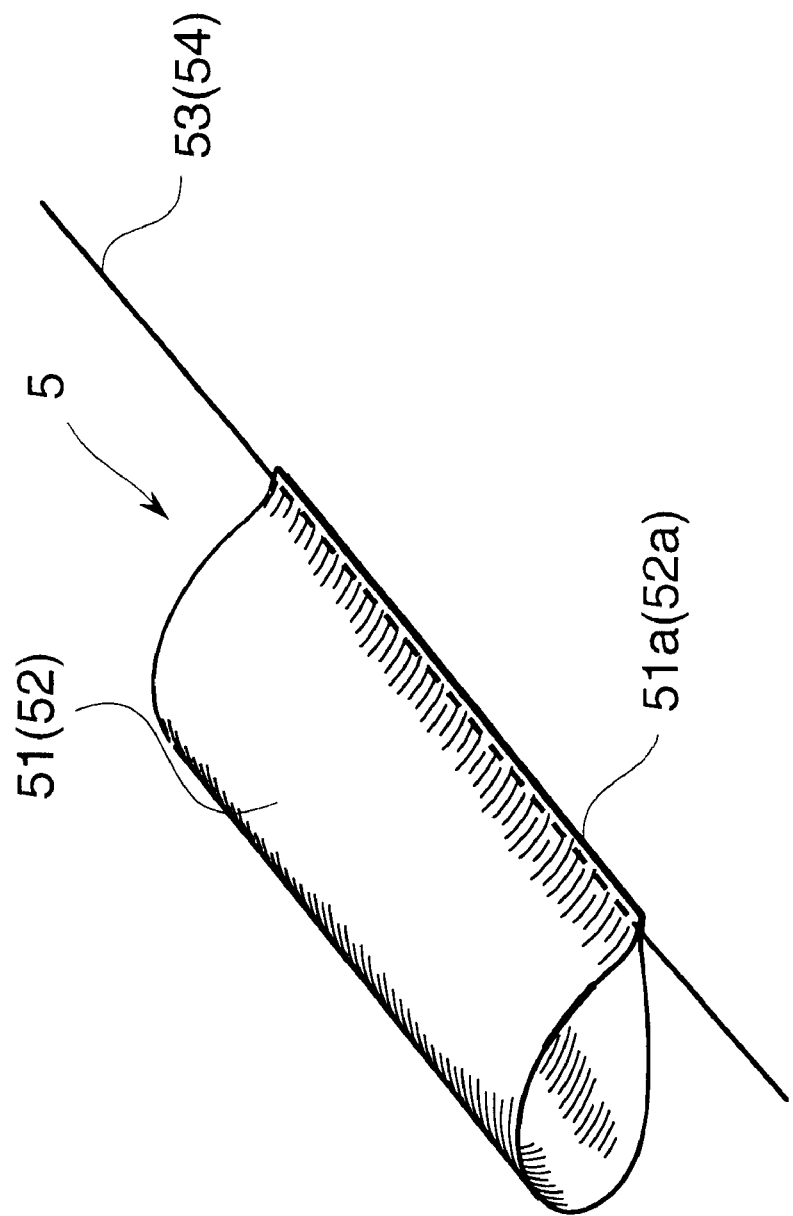
FIG. 4 is a perspective view of the collapsing device in a condition prior to being used.

The first wire 53 is flexible made of nickel titanium alloys. The first wire 53 holds the first wrapping member 51 in a shape of a tube as shown in FIG. 4 by steps of overlapping both edges 51a of the first wrapping member 51 so as to make the first wrapping member 51 in a shape of a general tube and passing the first wire 53 so as to sew the overlapped edges 51a together in broken lines. The second wire 54 is, like the first wire 53, to sew both edges 52a of the second wrapping member 54 together and a material thereof is the same as that of the first wire 53.

Then the artificial blood vessel 1 is contained in the first and second wrapping members 51 and 52 of the collapsing device 5 in a collapsed condition by the following steps. First, as shown in FIG. 5, prepare a pipe member 61 and a guide member 62 having a tapered guide portion having a smaller diameter and which can be passed through an internal space of the pipe member 61. A collapsing aid 63 is continuously arranged at one end 61a of the pipe member 61. Then the guide member 62 is inserted into the pipe member 61 through the end 61a until a side having the smaller diameter of the guide member 62 projects from the other end 61b, next the first wrapping member 51 which has been kept in a shape of a tube by the first wire 53 is mounted on the guide member 62 through the side of the smaller diameter of the guide member 62 in a condition that the other side having an ordinary size of a diameter of the guide member 62 is generally connected continuously with the other end 61b of the pipe member 61, and then the first wrapping member 51 is moved to slide along a tapered guide portion of the guide member 62 toward a direction of a bigger diameter of the guide member 62 as shown by an arrow in FIG. 5 so as to mount the first wrapping member 51 on the outer circumference of the pipe member 61 through the outer circumference of the guide member 62 at a position shown in FIG. 6. Finally, the guide member 62 is drawn from the end 61a of the pipe member 61 as shown by an arrow in FIG. 6.

Figure 8:
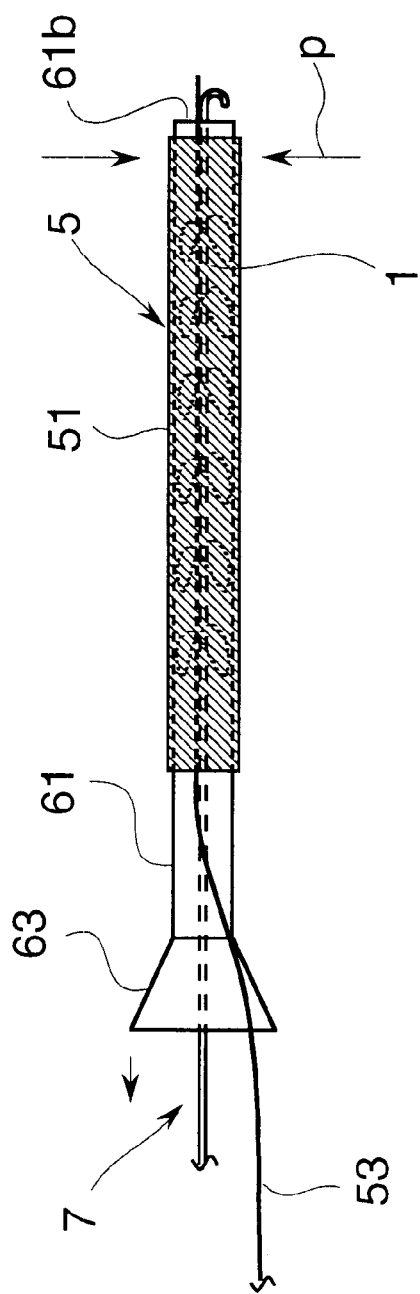
FIG. 8 is a view for explaining the procedure to collapse the artificial blood vessel with the collapsing device.
Figure 13:
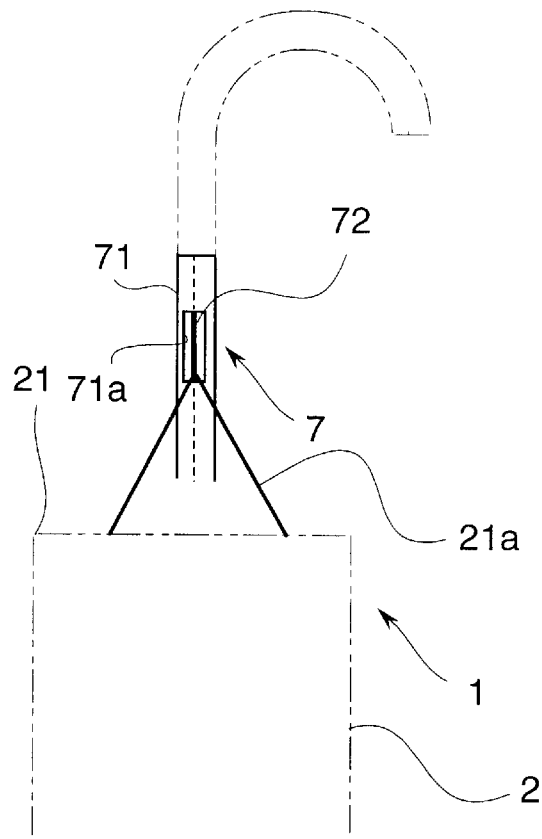
FIG. 13 is a schematic diagram showing a transporting device used in the embodiment.

Next, the artificial blood vessel 1 is inserted as shown in FIG. 7 into the pipe member 61 through the end 61a in a collapsed condition. For collapsing the artificial blood vessel 1 an inner face of the collapsing aid 63 is preferably used and for transporting the artificial blood vessel 1 in the pipe member 61 a transporting device 7 is used. The transporting device 7 is essentially for transporting the artificial blood vessel 1 to a target position inside a human body as shown in FIG. 16 through a sheath C, and so arranged that a wire 72 is contained in a tube 71 as shown in FIG. 13. The wire 72 is drawn out of the tube 71 through a window 71a of the tube 71 for engagement with a hooking means 21a attached to the front end ring member 21 and then drawn into the tube 71 again, thereby to make the transporting device 7 engage and hold the front end ring member 21. Then when the transporting device 7 is pushed toward a direction as shown by an arrow in FIG. 7, a front side of the artificial blood vessel 1 is hauled forward, which makes each of the ring members 21, 22, 23, 24 of the body portion 2 collapsed one by one into a wavy shape having a peak and a valley alternately and repeatedly along a circumferential direction along an inner face of the collapsing aid 63. Then the artificial blood vessel 1 is inserted into the pipe member 61 with the branch portion 3 attached thereto. Thus the artificial blood vessel 1 is introduced and inserted into inside of the pipe member 61 at a position which corresponds to the position at which the first wrapping member 51 is mounted as shown in FIG. 8. In stead of this procedure, a following procedure may be adopted; a front pull string is passed through the above-described hooking means 21a, both ends of the front pull string is passed through the pipe member 61 and the artificial blood vessel 1 is introduced into the pipe member 61 by pulling the front pull string.

Figure 9:
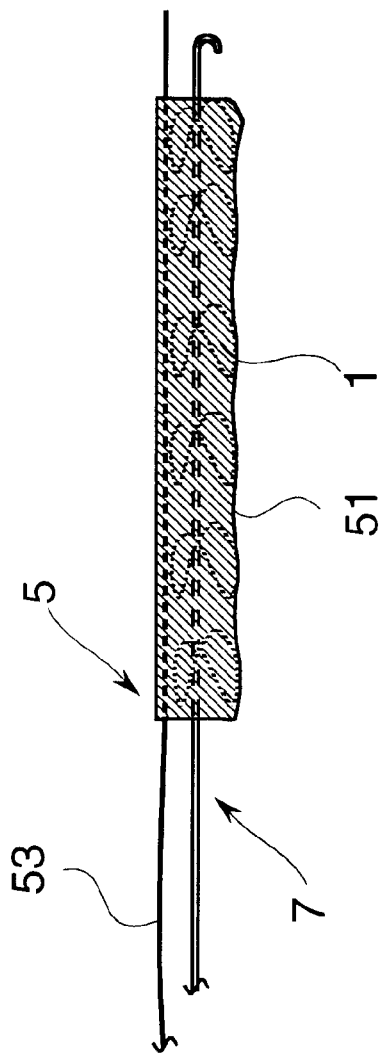
FIG. 9 is a view for explaining the procedure to collapse the artificial blood vessel with the collapsing device.

Then the wrapping member 51 and the artificial blood vessel 1 are restricted from moving by picking the wrapping member 51 and a part of the artificial blood vessel 1 together with a finger at a position shown by an arrow p in FIG. 8. With this condition kept, the pipe member 61 is moved rearward relatively to the position so as to draw the wrapping member 51 and the artificial blood vessel 1 out of the pipe member 61. Then the artificial blood vessel 1 is being inserted into inside of the wrapping member 51. Finally, the artificial blood vessel 1 is contained in the wrapping member 51 in a collapsed condition by drawing out the pipe member 61 completely as shown in FIG. 9. Although the branch portion 3 is not illustrated in FIGS. 5, 6, 8 and 9, the branch portion 3 is contained in the wrapping member 51 together.with the body portion 2.

Figure 10:
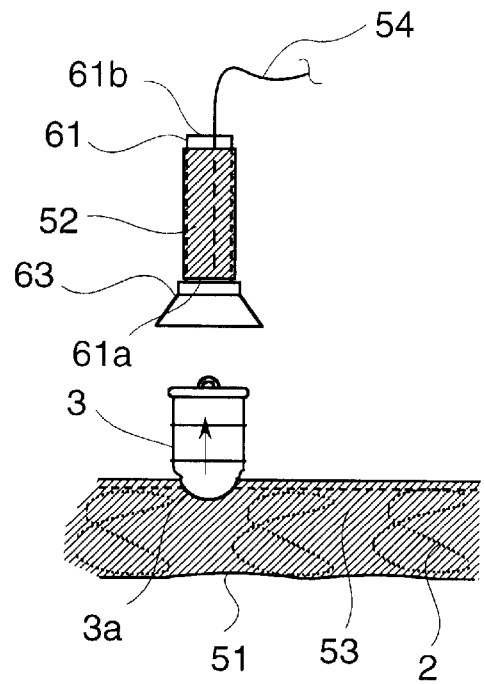
FIG. 10 is a view for explaining the procedure to collapse the artificial blood vessel with the collapsing device.
Figure 11:
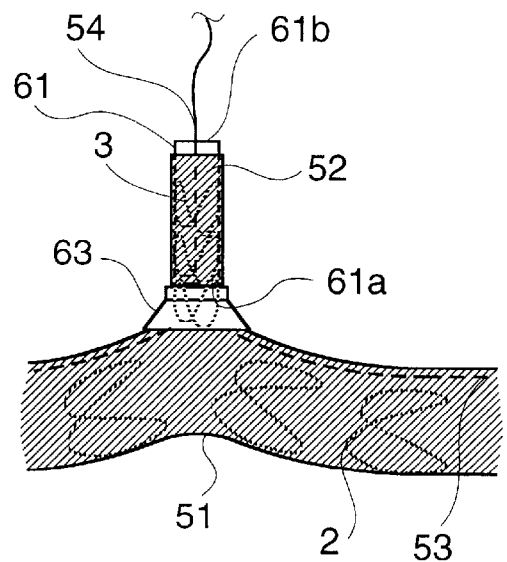
FIG. 11 is a view for explaining the procedure to collapse the artificial blood vessel with the collapsing device.
Figure 12:
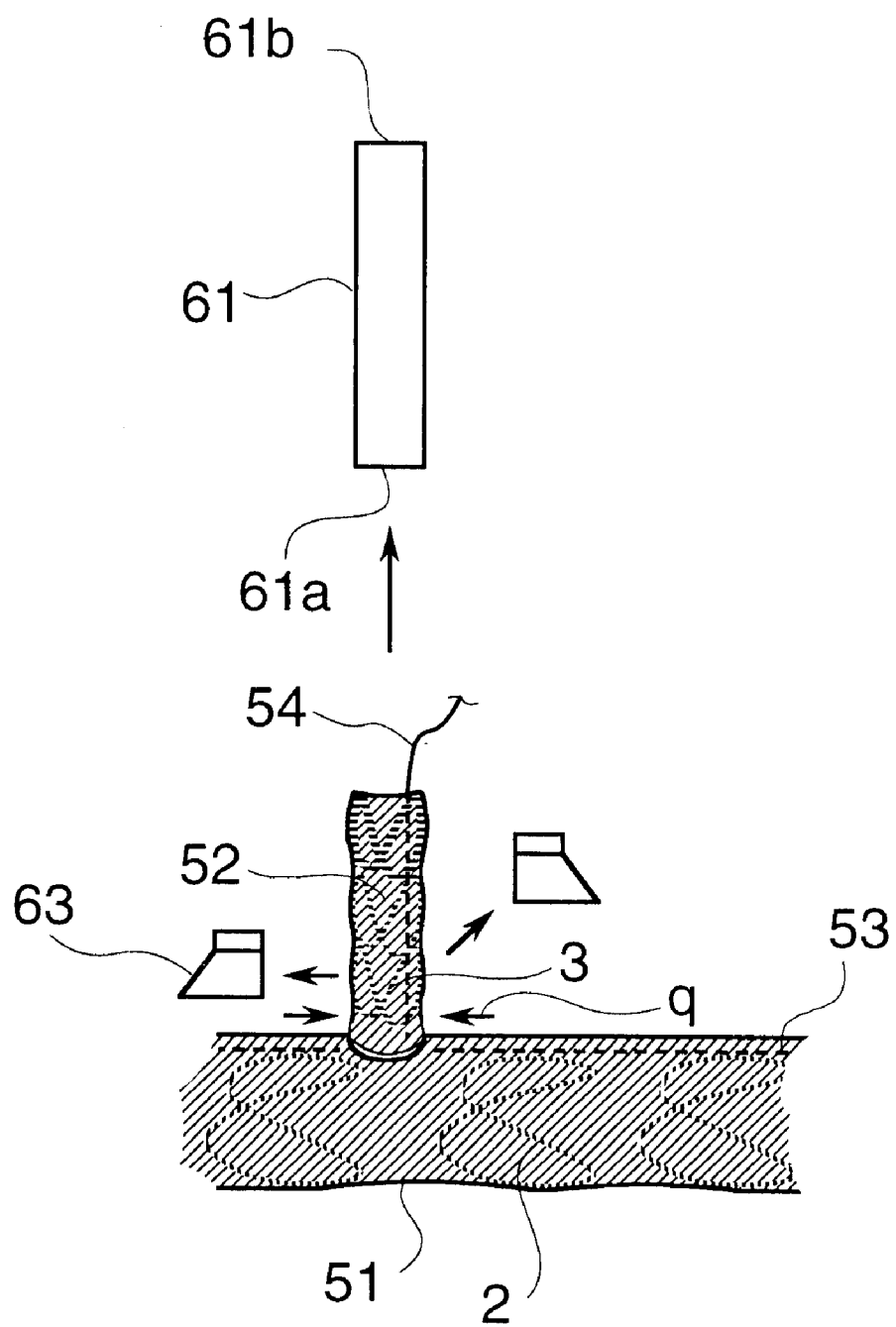
FIG. 12 is a view for explaining the procedure to collapse the artificial blood vessel with the collapsing device.

Next, the branch portion 3 is wrapped by means of the second wrapping member 52 and the second wire 54. In order to wrap the branch portion 3, a part of seams in the first wrapping member 51 sewed by the first wire 53 is pushed to make an opening wider and the branch portion 3 is introduced outside through the opening in the the first wrapping member 51 as shown by an arrow in FIG. 10. The second wrapping member 52 is mounted on the outer circumference of the pipe member 61 to which a funnel-shaped collapsing aid 63 is attached in a same manner as mentioned above and the branch portion 3 is contained in the pipe member 61 as shown in FIG. 11. In containing the branch portion 3 into the pipe member 61 through the collapsing aid 63, the pipe member 61 may be picked to draw through the other end 61b by the use of forceps or may be drawn by the use of a string for a front pull which has been passed through a hooking means 31a like a case described above because the pipe member 61 is short. In this case, since the base end 3a of the branch portion 3 is connected with the body portion 2, it is not possible for the pipe member 61 to be drawn together with the collapsing aid 63 through the other end 61b as it is. Considering this arrangement, the branch portion 3 is contained in the wrapping member 52 in a collapsed condition of a wavy shape by the following steps; the branch portion 3 is inserted into the pipe member 61 through the collapsing aid 63, the collapsing aid 63 is removed so as to release one end 61a of the pipe member 61, as shown in FIG. 12, by resecting the collapsing aid 63 or something like that and the pipe member 61 is drawn out with the second wrapping member 52 and the branch portion 3 restrained from moving as shown by an arrow q in FIG. 12. If the collapsing aid 63 is made of a relatively flexible material and can be shrunk as a same size as that of the pipe member 61, it can be separated from the second wrapping member 52 without being broken like the above.

Figure 2:
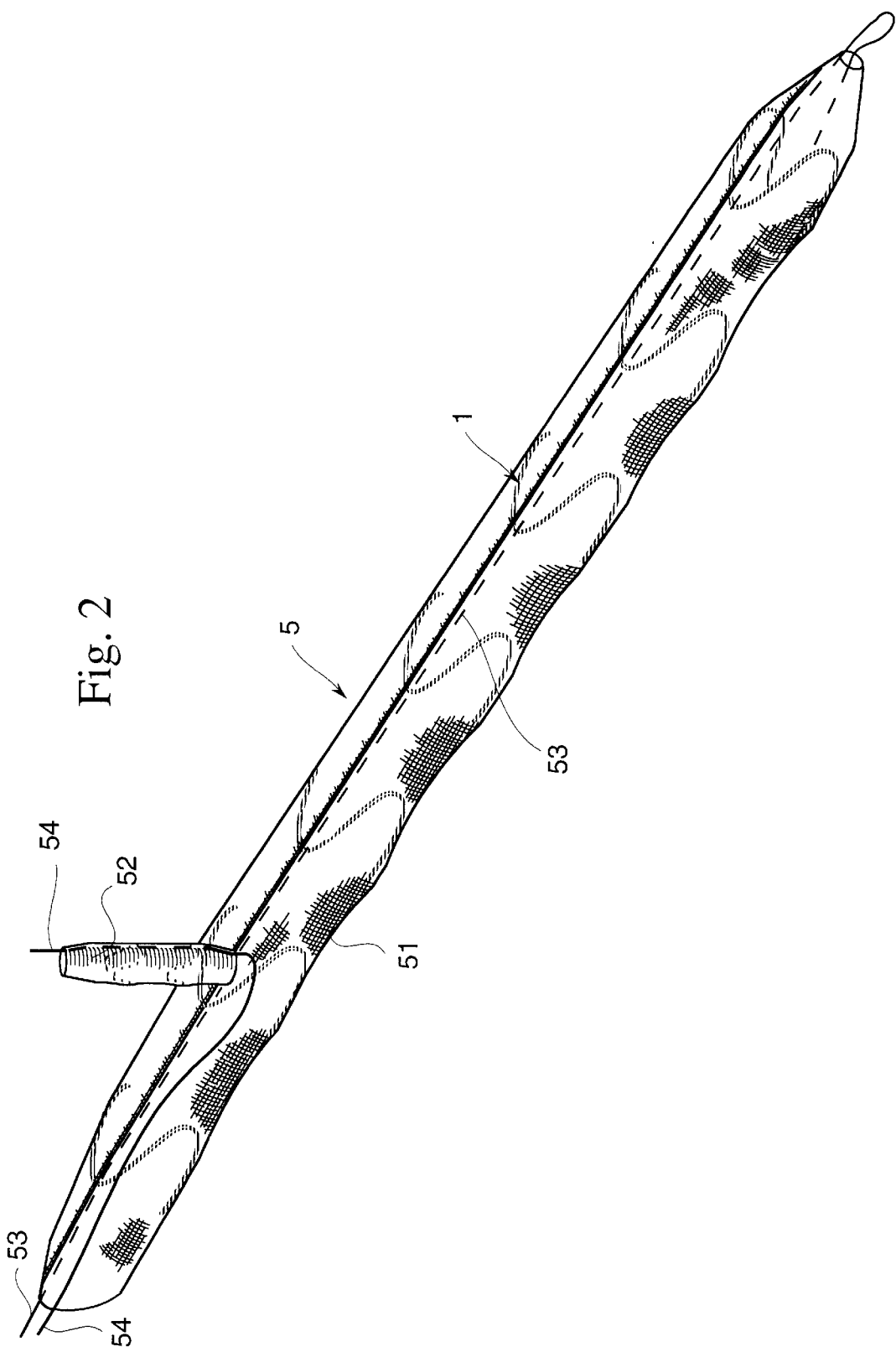
FIG. 2 is a perspective view of the branched artificial blood vessel in a collapsed condition by means of the collapsing device of the invention.

FIG. 2 shows the artificial blood vessel 1 which has been collapsed by the use of the collapsing device 5 in the above manner. Next, a procedure of introducing the artificial blood vessel 1 into the human body will now be explained. For introducing the artificial blood vessel 1 used are a hauling device 8 which tows the rear end of the body portion 2 rearward and a secondary hauling device 9 which brings the branch portion 3 from the trunk blood vessel 41 to the branch blood vessel 42 as well as the above described transporting device 7.

Figure 14:
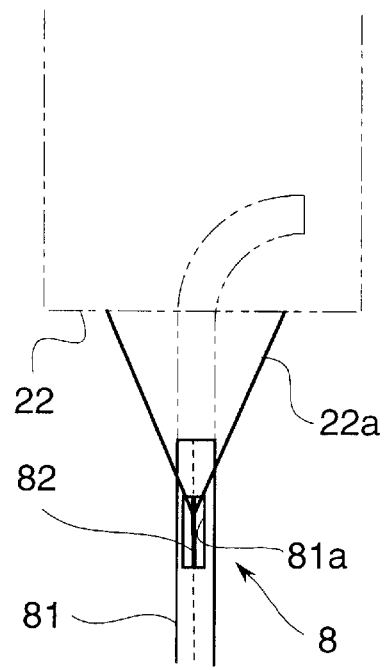
FIG. 14 is a schematic diagram showing a hauling device used in the embodiment.

The hauling device 8 is, as shown in FIG. 14, so arranged that a wire 82 is contained in a tube 81 and holds and makes an engagement with the end ring member 22 by engaging the wire 82 which is drawn out of a window 81a provided on the tube 81 with a hooking means 22a provided on one part of the end ring member 22 locating rear and then drawing the wire 82 into the tube 81 again. The hauling device 8 can haul the body portion 2 of the artificial blood vessel 1 toward a opposite direction to a direction the hauling device 7 does.

Figure 15:
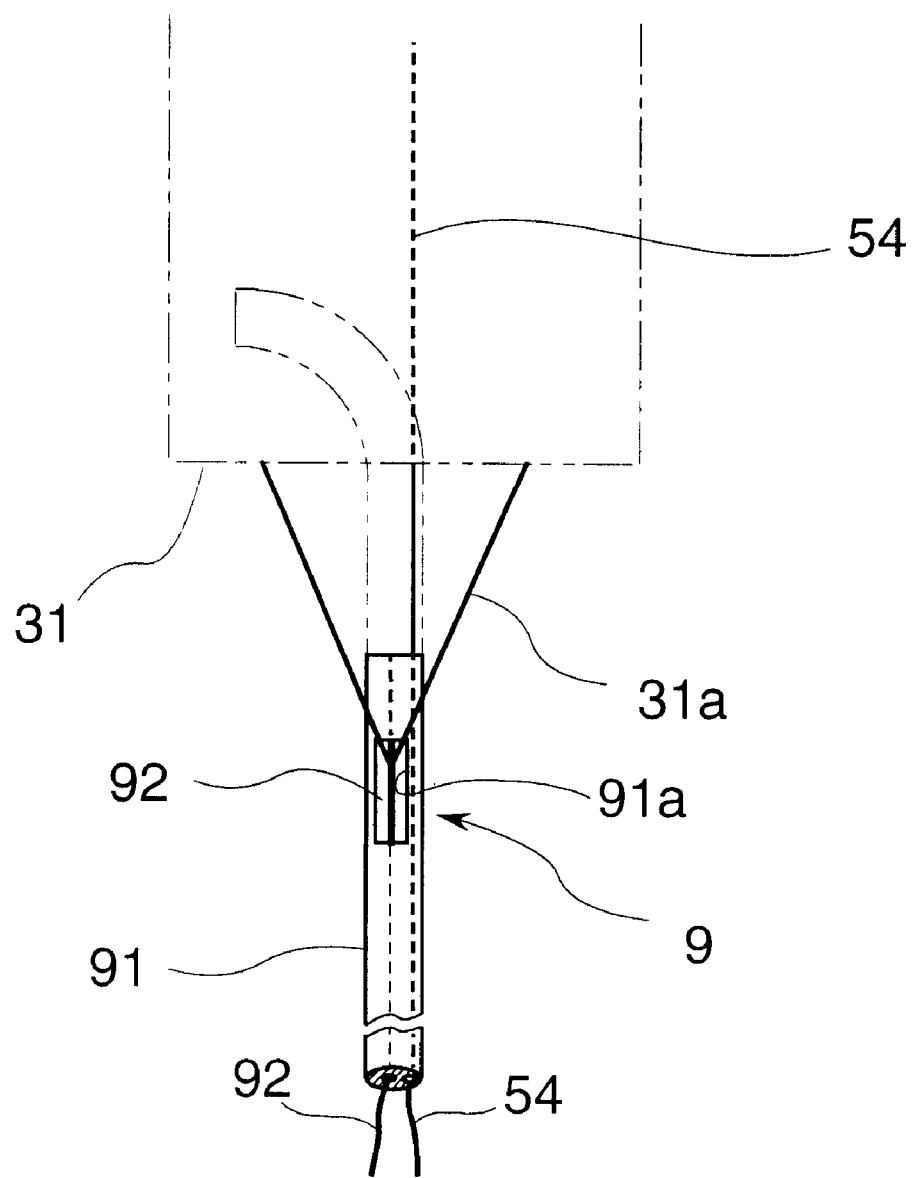
FIG. 15 is a schematic diagram showing a secondary hauling device used in the embodiment.

The secondary hauling device 9 is, as shown in FIG. 15, so arranged that a wire 92 is contained in a tube 91 and holds and makes an engagement with the end ring member 31 of the branch portion 3 by engaging the wire 92 which is drawn out of a window 91a provided on the tube 91 with the hooking portion 31a provided on one part of the end ring member 31 and then drawing the wire 92 into the tube 81 again. The secondary hauling device 9 can haul whole of the branch portion 3 of the artificial blood vessel 1 toward a direction to be separated from the body portion 2. The tube 91 has an arrangement of double-lumen so as to contain both the wire 92 and the wire 54 of the collapsing device 5. Especially the tube 91 of the secondary hauling device 9 used in this embodiment is made of a material which is more flexible than that of which the transporting device 7 and the hauling device 8 are made. In addition, at least the length corresponding to a distance from a groin of a thigh to the affected portion of the base end $b_{3a}$ of the secondary hauling device 9 is made of a guide member $b_{3x}$ such as a helical spring which is not only flexible but also having a characteristic that a force can be so transmitted to the whole part thereof by manipulating one part thereof that the secondary hauling device 9 can be freely rotated, inserted or pulled. The base end $b_{3a}$ is bent sideward along the length thereof, which makes it possible to change a direction of the base end $b_{3a}$ relatively big by manipulating the guide member $b_{3x}$ of the secondary hauling device 9.

Then introduce the devices 7, 8 and 9 into a human body through the sheath C having a sealing mechanism cs at a base end thereof.

Especially the secondary hauling device 9 is not introduced into the sheath C through the sealing mechanism cs by itself but is introduced into the sheath C in a condition of being contained in a guide pipe H. In other word, the secondary hauling device 9 is contained in the guide pipe H in a condition of being folded to be double and so arranged that a portion of being folded to be a loop is introduced outside through a base end of the guide pipe H and both ends of the secondary hauling device 9 are introduced outside of the guide pipe H through a front end of the guide pipe H. At the base end $h_1$ of the guide pipe H also provided is a sealing mechanism hs.

Next, a procedure to implant the artificial blood vessel 1 will be explained. First, the sheath C is inserted into inside of a human body from an inguinal artery at a groin F of a thigh, as shown in FIG. 16, until a tip of the sheath C is positioned near an affected portion where an aortic aneurysm 43 or the like is caused. Then the artificial blood vessel 1 collapsed by the collapsing device 5 of the invention is introduced into the sheath C together with the transporting device 7 and the hauling device 8. At the same time the secondary hauling device 9 is inserted into the sheath C through the guide pipe H. Next, the transporting device 7 is pushed so as to transport the artificial blood vessel 1 accompanied by the hauling device 8 and the secondary hauling device 9 attached thereto to a target position where the branch blood vessel 42 branches from the trunk blood vessel 41 as shown in FIG. 16. Subsequently, the artificial blood vessel 1 is released from the sheath C. Since the artificial blood vessel 1 is kept in a collapsed condition by the use of the collapsing device 5 of the invention after released, it does not necessarily have to be released at a predetermined location.

Figure 17:
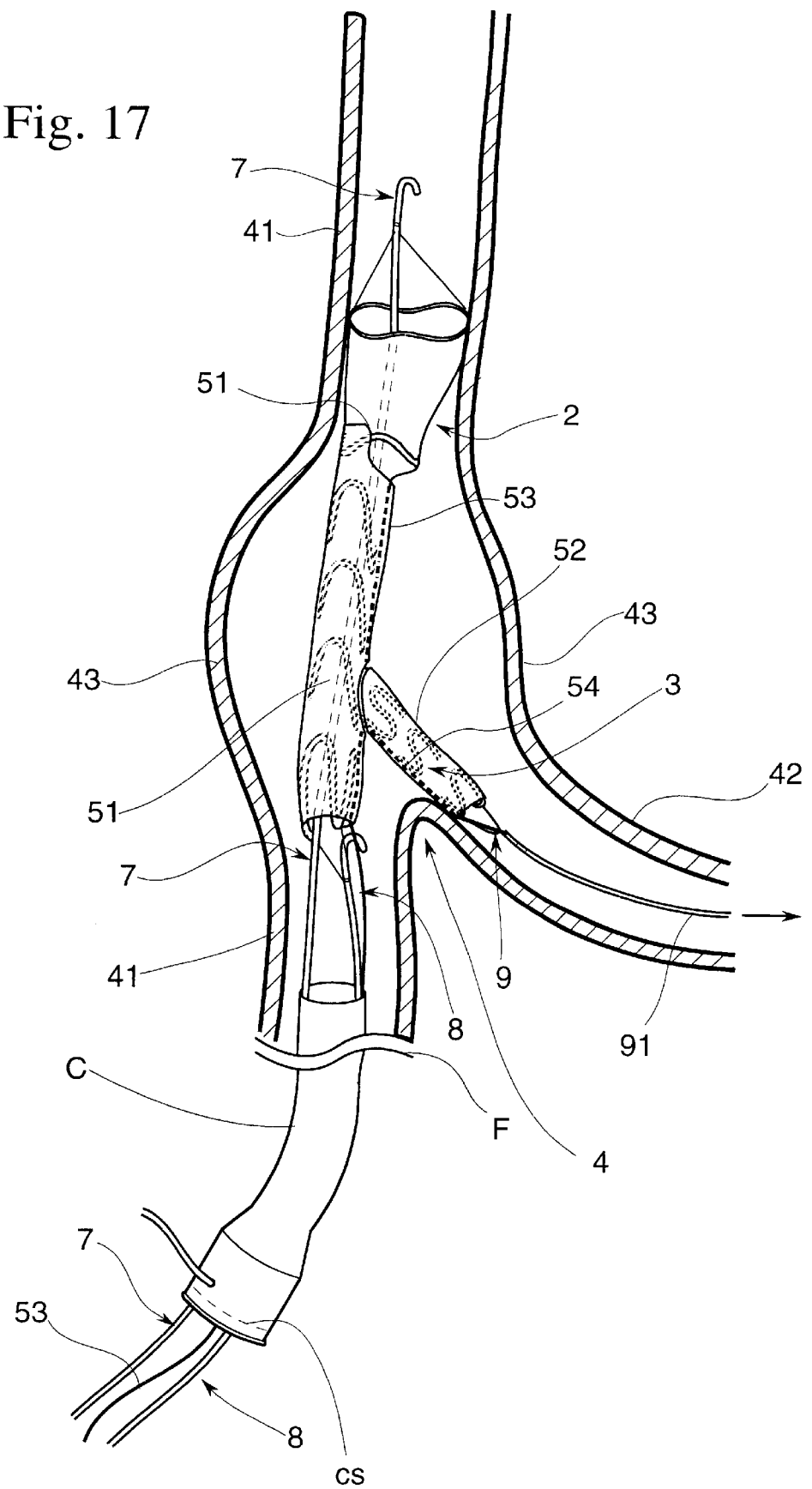
FIG. 17 is a view for explaining the procedure to implant the artificial blood vessel of the embodiment into the target position.

Under the condition, a catcher G is introduced near the affected portion through a catheter K from another bifurcated portion of the groin in order to catch the secondary hauling device 9. The catcher G comprises a wire g1 at a front tip of which a loop is formed and a tube g2 in which the wire g1 is contained, and is so constructed that the loop projecting out of the tube g2 opens or closes if the wire g1 is drawn out of the tube g2 or inserted into the tube g2. The base end $b_{3a}$ of the secondary hauling device 9 is caught by the use of the wire g1 which has the loop by operating the guide member $b_{3x}$ of the secondary hauling device 9 and the catcher G. As mentioned above, near the base end $b_{3a}$ of the secondary hauling device 9 is made to be bent to facilitate an operation of catching. This makes it possible for the base end $b_{3a}$ to be freely rotated, inserted or pulled by manipulating the guide member $b_{3x}$ which is drawn out of the guide pipe H. After catching the base end $b_{3a}$ by the use of the catcher G, the base end $b_{3a}$ is drawn out of the human body through the other groin of the thigh. The longer the base end $b_{3a}$ is drawn, the shorter a length of the secondary hauling device 9 locating out of the sealing mechanism hs of the guide pipe H becomes. Finally, the secondary hauling device 9 is contained in the guide pipe H after passing through the sealing mechanism hs. Then the base end $b_{3a}$ of the secondary hauling device 9 is gradually drawn out of the human body through the other groin of the thigh. As shown in FIG. 17, the front tip of the secondary hauling device 9 alone is eventually left in the human body and the base end $b_{3a}$ is almost completely drawn out from the other groin of the thigh. Then after the secondary hauling device 9 is drawn out, the branch portion 3 of the artificial blood vessel 1 is hauled toward a direction shown by an arrow in FIG. 17 by the use of the secondary hauling device 9 so as to be placed at an appropriate position at the branch blood vessel 42 which branches from the trunk blood vessel 41.

Figure 18:
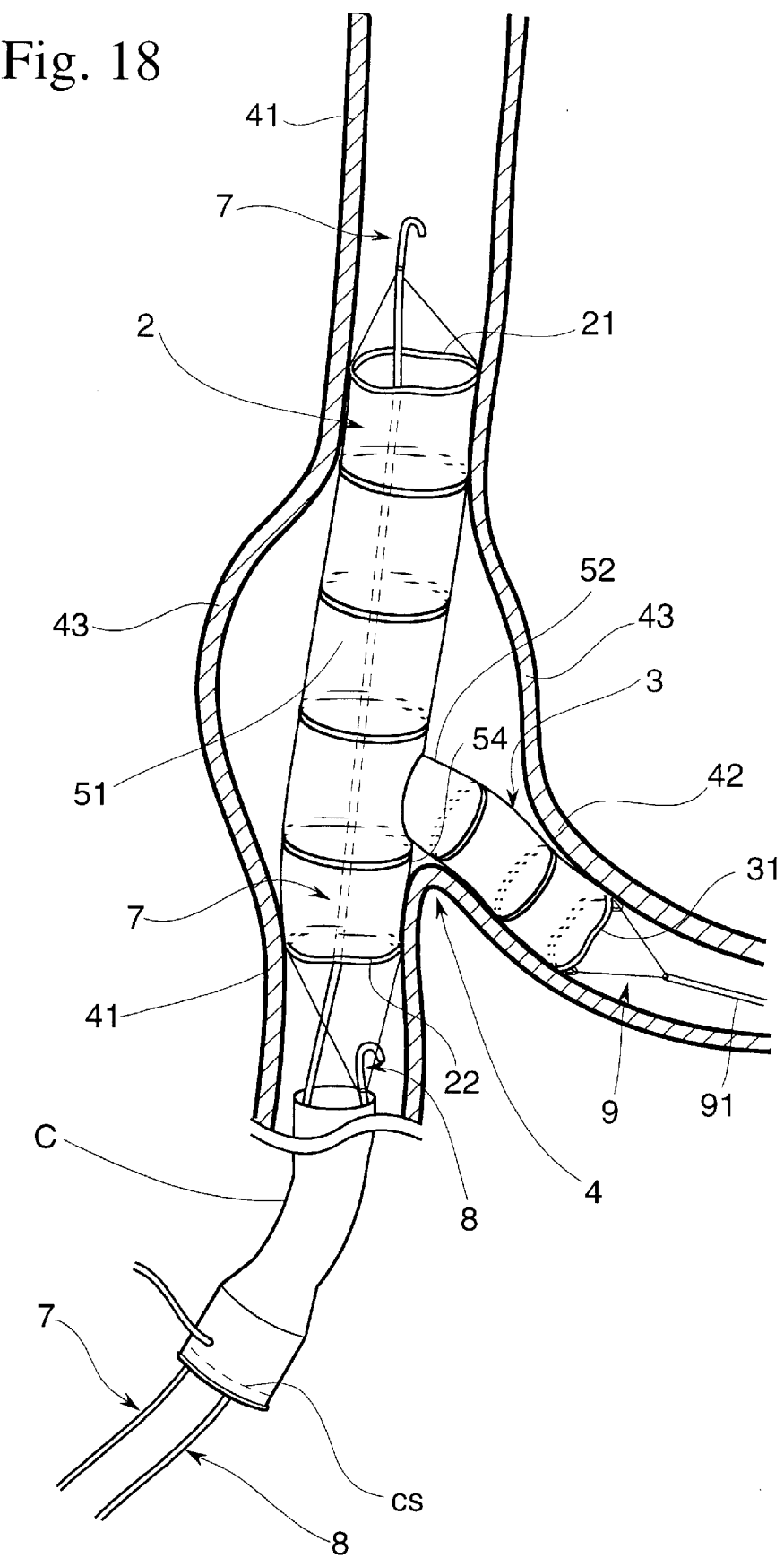
FIG. 18 a view for explaining the procedure to implant the artificial blood vessel of the embodiment into the target position.

After the artificial blood vessel 1 is arranged at the appropriate position, the wires 53 and 43 which constitute the collapsing device 5 of the embodiment are drawn. More concretely, first the first wire 53 is drawn so as to release the first wrapping member 51 from the body portion 2 and each portion of the body portion 2 is restored to be inflated one by one so as to tightly attach to an inner wall of the trunk blood vessel 41 by making use of elasticity. Next, the second wire 54 is drawn so as to release the second wrapping member 52 from the branch portion 3 and each portion of the branch portion 3 is restored to be inflated one by one so as to tightly attach to an inner wall of the branch blood vessel 42 by making use of elasticity. FIG. 18 shows a condition in which each of the body portion 2 and the branch portion 3 of the artificial blood vessel 1 is attached to the trunk blood vessel 41 and the branch blood vessel 42 respectively. A state in which each of the ring members 21, 22 and 31 is not restored into a shape of round as shown in FIG. 18 is due to pulsations of a blood vessel with which each of the ring members 21, 22 and 31 comply. The body portion 2 and the branch portion 3 is released from an engagement with each of the wires 72, 82 and 92 of the transporting device 7, the hauling device 8 and the secondary hauling device 9 by drawing the wires 72, 82 and 92. Finally, the transporting device 7, the hauling device 8 and the secondary hauling device 9 are drawn out of the human body. This will complete implantation of the artificial blood vessel 1 into the target portion. The first and second wrapping member 51, 52 which has been separated may be left at the separated position and only the first and second wires 53, 54 may be removed, however, the wrapping member 51, 52 may be removed by capturing it, if necessary.

As mentioned above, the collapsing device 5 for artificial blood vessels in accordance with the embodiment comprises the wrapping members 51 and 52 which are generally flat when spread and the wires 53 and 54 which hold each of the wrapping members 51, 52 in a condition of being rolled into a shape of a tube, and is so arranged that the artificial blood vessel 1 is contained in the wrapping members 51 and 52 held by the wires 53 and 54 in a collapsed condition and the wires 53 and 54 are separated from the wrapping members 51 and 52 at the target position to spread the wrapping members 51 and 52 so as to release the artificial blood vessel 1.

In accordance with the collapsing device of the invention, since whole of the artificial blood vessel 1 is contained inside the tubular wrapping member 51 and 52, it is possible to reduce protuberance which is generated locally on an outer face of the artificial blood vessel 1 compared with a case in which the artificial blood vessel 1 is bound with a string partially to keep a collapsed condition. In addition, if the artificial blood vessel 1 is released from a condition of being held by the wires 53, 54 at a target position, the wrapping member 51, 52 is spread and a space surrounding the collapsed body portion 2 and the collapsed branch portion 3 of the artificial blood vessel 1 will be open wide. As a result, interference with a movement of restoring the artificial blood vessel 1 into a predetermined shape can effectively be avoided.

Especially, if the wrapping member 51, 52 is made of an expansible material, the material of the wrapping member 51, 52 stretches so as to wrap the artificial blood vessel. 1 effectively when the wrapping member 51, 52 is held to wrap the artificial blood vessel 1 whereas the material of the wrapping member 51, 52 shrinks so as to be quickly separated from the body portion 2 or the branch portion 3 and move to a certain position near the target position, although not shown in FIG. 18, when the wrapping member 51, 52 is released from a condition of being held.

In addition, since the material of the wrapping member 51, 52 is in a shape of a mesh, a stretching properties can effectively be demonstrated because a cross of the mesh stretches or shrinks.

Further since the mesh is woven with wefts and warps, a stretching properties can sufficiently be demonstrated along both of lengthwise and crosswise and a cross of the mesh is hard to be moved as well as hard to be loosened, thereby to especially produce the above-mentioned effects for certain.

More specifically since the material of the wrapping member 51, 52 is made of polyurethane fibers, it is easy to provide the material with a stretching properties, in addition, the wrapping material 51, 52 can be left at a target portion in a human body together with the artificial blood vessel 1 after released because polyurethane fibers are not harmless to a human body.

In addition, since the wire 53, 54 is a wire rod and the overwrapped edges 51a and 52a of the wrapping member 51, 52 are sewed by the wire 53, 54, it is possible to keep the wrapping member 51, 52 in a shape of a tube as well as to release a condition of the wrapping member 51, 52 being held directly with relatively little resistance by pulling the wire 53, 54 lengthwise.

Especially since the wire 53, 54 is made of nickel titanium, it is possible to obtain an extremely flexible elasticity, it is possible for the wire 53, 54 to pass through a bent portion in a human body so as to reach an target position. In addition, even though whole of the wire 53, 54 gets twisted, it can be expected that the wire 53, 54 is corrected by itself due to its elasticity. Further, since a length of the wrapping member 51, 52 can be adjusted depending on a demand because it is possible to cut only the wrapping member 51, 52 along a direction at right angles generally to the wire 53, 54 in a condition of passing the wire 53, 54 therethrough without cutting the wire 53, 54, if necessary. Further, if the wrapping member 51, 52 is sewed with a thread, the thread might get entangled. However, since the wrapping member 51, 52 is sewed with the above-mentioned wire 53, 54, there is no fear of getting entangled like the thread.

Since the collapsing device 5 of this embodiment has the above arrangement, it is extremely suitable for collapsing the artificial blood vessel 1. More specifically, the artificial blood vessel 1 is so arranged that ring members 21, 22, 23, 24 arranged intermittently are bridged by the cover 20 and each of the ring members 31 32 is collapsed into a wavy shape having a peak and a valley alternately and repeatedly along a circumferential direction thereof. Then protuberance is likely made locally on outer faces of the ring members 21, 22, 23, 24 31, 32 due to elastic restoring force when the artificial blood vessel 1 is collapsed. However, with the collapsing device 5 of the invention, whole of the body portion 2 and the branch portion 3 of the artificial blood vessel 1 are wrapped by the wrapping member 51, 52 and kept in a collapsed condition. As a result, it is possible to firmly press down protuberance, thereby to form a smooth curved surface of the outer face thereof.

Since the method of using the collapsing device 5 of this embodiment comprises steps of mounting the wrapping member 51 on near an end portion of an outer circumference of a pipe member 61, inserting the artificial blood vessel 1 into inside of the pipe member 61 and drawing the wrapping member 51 and the body portion 2 of the artificial blood vessel 1 are simultaneously out of the pipe member 61 in a condition that both of the wrapping member 51 and the body portion 2 of the artificial blood vessel 1 are restrained from moving interactively at the end portion, it is possible to contain the artificial blood vessel 1 inside the wrapping member 51 in an appropriate collapsed condition through simple procedures, even though the wrapping member 51 is highly elastic and the artificial blood vessel 1 is highly elastically restorable.

Especially since the artificial blood vessel 1 has the branch portion 3, the artificial blood vessel 1 is collapsed with the procedure of collapsing the body portion 2 by using the first wrapping member 51 and the wire 53, releasing a part of the first wrapping member 51 from a condition of being held by the wire 53, drawing the branch portion 3 out out the first wrapping member 51 through the part and collapsing the branch portion 3 by using the second wrapping member 52 and the wire 54. As a result, it is possible to keep the body portion 2 and the branch portion 3 in an appropriate collapsed condition respectively without causing a big inconvenience although the artificial blood vessel 1 has the branch portion 3.

Further, since the wrapping member 51, 52 is mounted on an outer circumference of the pipe member 61 along a tapered guide portion to open wider gradually, it is possible to move the wrapping member 51, 52 to the outer circumference of the pipe member 61 so as to be mounted thereon with ease and securely even if a shrinkage degree of the wrapping member 51, 52 is so high that the wrapping member 51, 52 shrinks quite a lot.

In addition, with a procedure of transporting the artificial blood vessel 1 to a target position, restoring the artificial blood vessel 1 into a predetermined shape by releasing the wrapping member 51, 52 from a condition of being held by the wire 53, 54 and then removing only the wire 53, 54 from the target position with the wrapping member 51, 52 left at the position together, it is not necessary to remove the wrapping member 51, 52. As a result, a procedure of transporting the artificial blood vessel 1 can be simplified.

Figure 19:
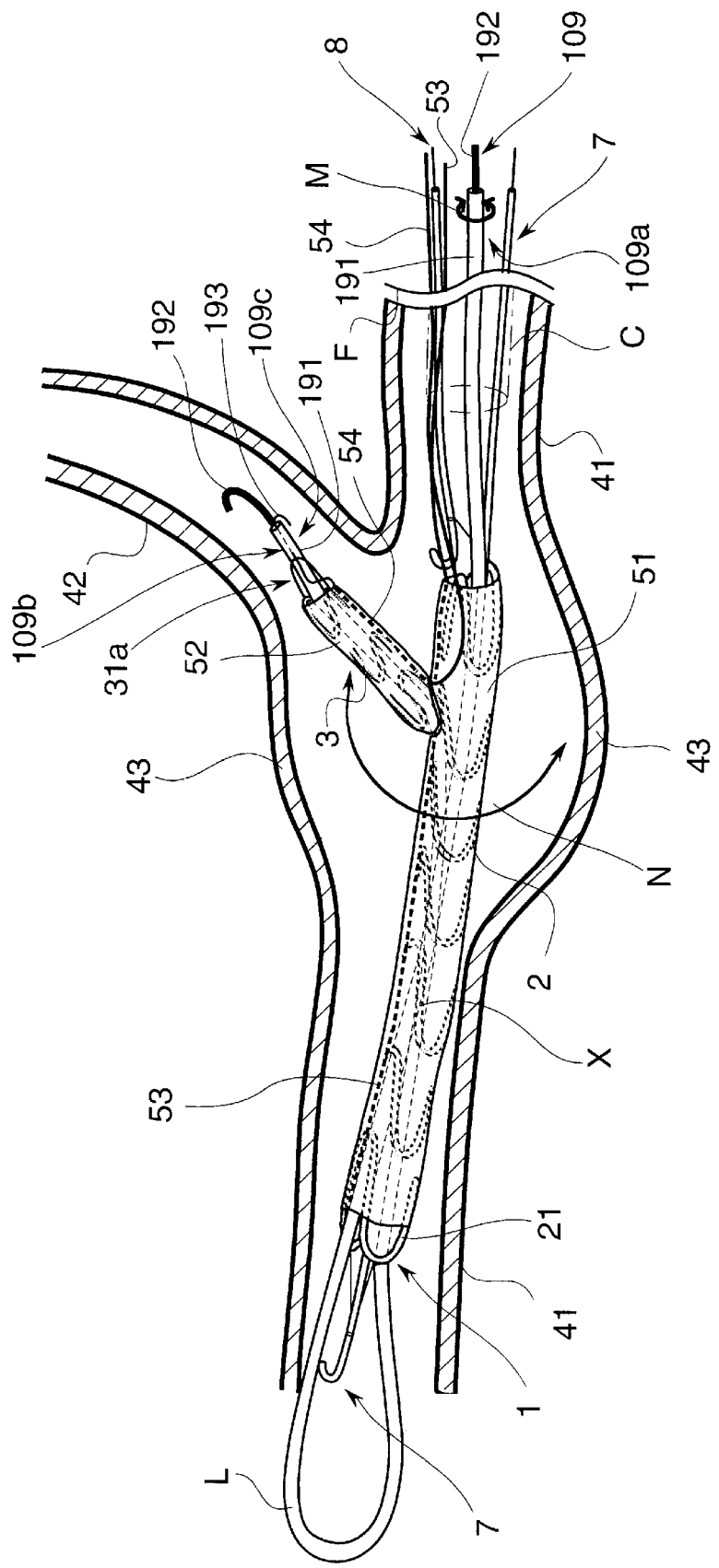
FIG. 19 is a view for explaining another method of implanting the artificial blood vessel.

For introducing the branch portion 3 into the branch blood vessel 42, if the branch blood vessel 42 branches toward an inner side to the surface of the human body and the catcher G can not be inserted, a guiding device 109 as shown in FIG. 19 may be used instead of the above-mentioned secondary hauling device 91. The guiding device 109 is operable for rotation by hand as indicated by an arrow M shown in FIG. 19 and comprises an operating rod 109a having a front end to be inserted into the body portion 2 from an opening end locating a base end thereof, a guiding rod 109b continuously connected to the operating rod 109a so as to be capable of turning around and having a front end extending to an opening end of the branch blood vessel 42, and a mooring means 109c for releasably mooring the branch portion 3 by a portion adjacent the opening end thereof to the guiding rod 109b and so arranged that the branch portion 3 accompanying the guiding rod 109b can be inserted into the branch blood vessel 42 together with the guiding rod 109b by moving the body portion 2 rearward when the guiding rod 109b has assumed a predetermined position by turning.

The operating rod 109a and the guiding rod 109b are formed of a flexible wire rod (usually called "catheter"). This wire rod is turned up to form a loop L, the base end side of which forms the operating rod 109a, the front side of which forms the guiding rod 109b. The front side and the base end side of the loop L are brought into contact with each other, and the contact portion X is fixed by tying with a string or the like. The loop L is so arranged that the most part thereof protrudes from the opening end of the body portion 2 defined by the ring member 21 locating front.

More specifically, the wire rod comprises a tube 191 and a guiding wire 192 retractably contained in the tube 191 with the front end of the guiding wire 192 protruding from the front end of the tube 191.

The mooring means 109c comprises a mooring wire 193 which alternatively restricts the hooking portion 31a of the branch potion 3 from moving in cooperation with the tube 191. The mooring means 109c is made to release a moored state of the hooking portion 31a with the branch portion 3 when the mooring wire 193 is drawn. Then the body portion 2 and the branch portion 3 are collapsed together with the guiding device 109 by the wrapping members 51 and 52 and the wires 53 and 54 like the above-described embodiment. The wire 54 serves also as the mooring wire 193.

Figure 20:
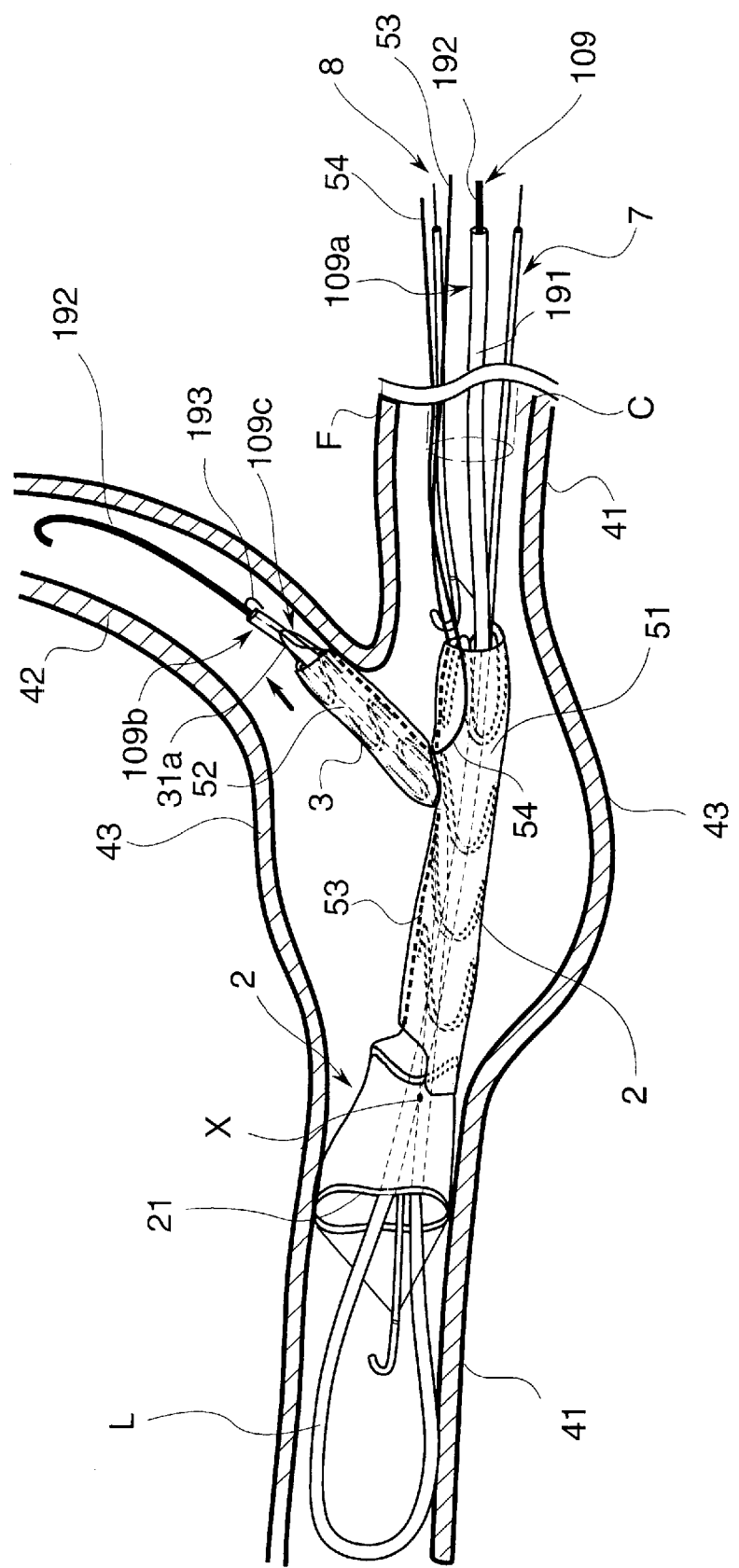
FIG. 20 is a view for explaining another method of implanting the artificial blood vessel.
Figure 21:
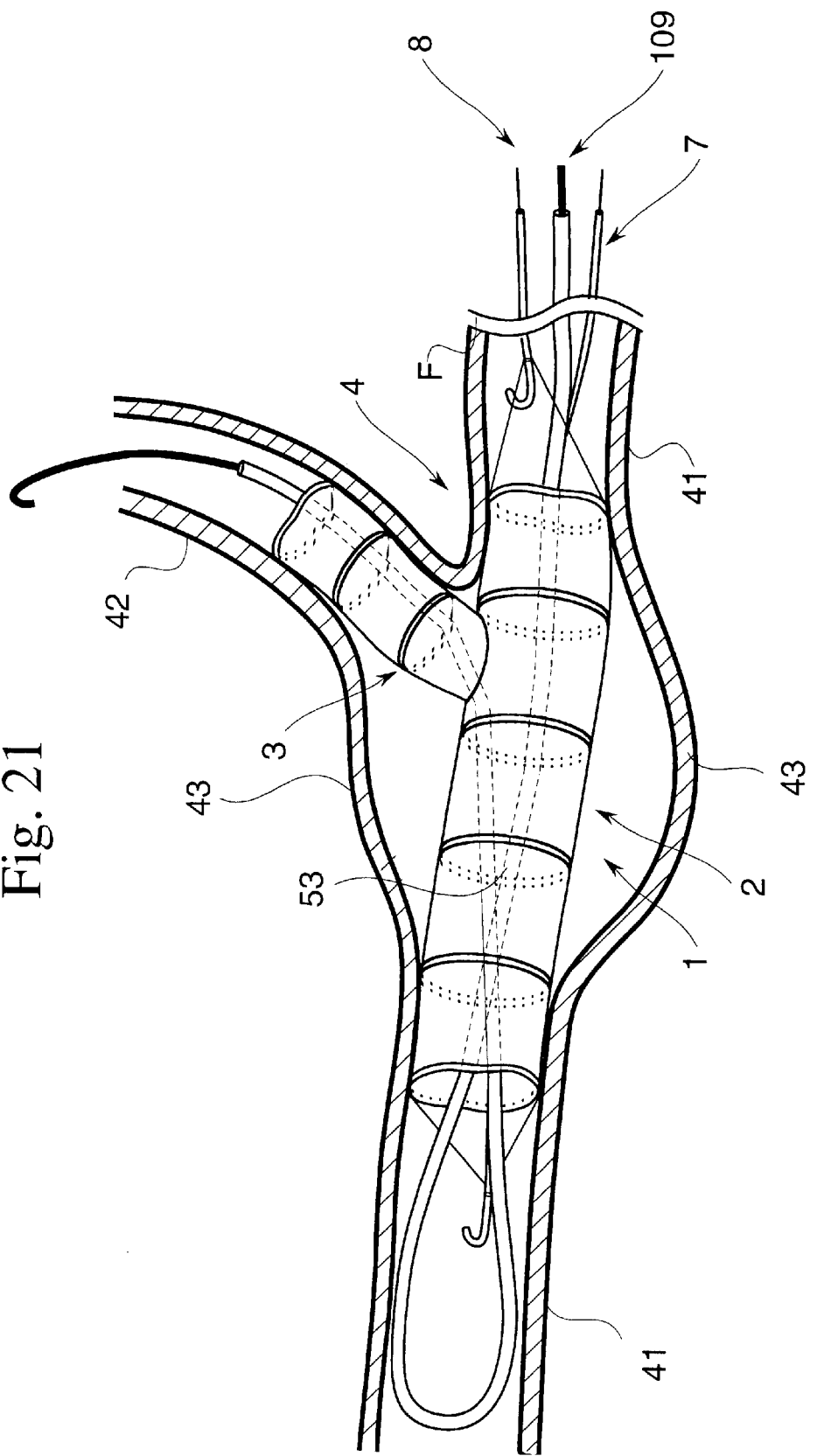
FIG. 21 is a view for explaining another method of implanting the artificial blood vessel.

For introducing the branch portion 3 into the branch blood vessel 42 by making use of the guiding device 109, the base end side of the tube 191 as the operating rod 109a is operated for rotation as indicated by the arrow M shown in FIG. 19 from the outside of the thigh F to cause the front side of the tube 191 as the guiding rod 109b to turn around as indicated by the arrow N shown in FIG. 19 so that the front end of the guiding rod 109b faces to the entrance of the branch blood vessel 42. The positioning of the guiding rod 109b may be achieved while observing the guiding rod 109b by X-raying or the like. Once the positioning is done, the guiding wire 192 is pushed forward so that the frond end thereof is first inserted into the branch blood vessel 42 as shown in FIG. 20. Thereafter, the hauling device 8 attached to the body portion 2 is pulled to move whole of the artificial blood vessel 1 backward. At this time, the guiding rod 109b forming the front side of the tube 191 advances in the direction indicated by an arrow shown in FIG. 20 to a predetermined location in the branch blood vessel 42 as accompanied by the branch portion 3 under the guidance of the guiding wire 192. When the branch portion 6 has reached the predetermined location and the branched artificial blood vessel 1 has wholly become in position, the wire 53 accompanying the body portion 2 is first pulled to separate the wrapping member 52 as shown in FIG. 20 and then the wire 54 accompanying the branch portion 3 is pulled to separate the wrapping member 53. This makes each of the body portion 2 and the branch portion 3 swell by making use of elasticity to be restored into a state to tightly attach to the trunk blood vessel 41 and the branch blood vessel 42 as shown in FIG. 21.

Finally, the wires 72 and 82 of the transporting device 7 and the hauling device 8 are pulled to release an engagement with the ring members 21 and 22, and the transporting device 7 and the hauling device 8 are moved out of the bifurcated portion 4. In addition, when the wire 54 which serves as the wire 193 also is pulled, the mooring means 9c is released, then the guiding device 9 also can be removed. Thus the branched artificial blood vessel 1 can preferably be released from a collapsed condition in a bifurcated portion 4 and can preferably be implanted.

The invention is not limited to the above-mentioned embodiment. For example, in the above embodiment the wrapping member which constitutes the collapsing device is sewed by a single collapsing device, but the body portion of the artificial blood vessel may be sewed and collapsed by a plurality of collapsing devices and each of the collapsing devices is separated one by one so as to restore the body portion. In accordance with the arrangement, the body portion of the branched artificial blood vessel can be appropriately collapsed avoiding the branch portion and the branch portion can be preferably collapsed because it becomes unnecessary to draw the branch portion out of an opening between seams like the above embodiment. In this case, it is effective to commonize a wire alone. More specifically, it is possible to commonize a wire with ease if the artificial blood vessel is sewed with separate tubes divided front and rear by the branch portion, a common wire is passed through both tubes and then the tubes are removed. In addition, if a plurality of wires are used, a resistance becomes low when drawn. As a result, this arrangement will be effective especially for a case in which drawing force exerts a harmful influence on a shape of the entire artificial blood vessel.

In the above embodiment the wrapping member of the collapsing device is separated starting from a front side locating upstream of the artificial blood vessel by drawing the wire, but may be separated starting from a base side locating downstream of the artificial blood vessel by reversing a direction to which the wire is inserted. In accordance with the arrangement, the artificial blood vessel is restored gradually from a side of downstream so as to be fixed to the inner wall of the blood vessel. Then it can be prevented that high fluid pressure is applied to a portion which meets a blood flow between a restored portion and a not-restored portion unlike a case in which the artificial blood vessel is restored from a side of upstream. As a result, it becomes possible to avoid a case in which the artificial blood vessel is carried downstream.

Figure 22:
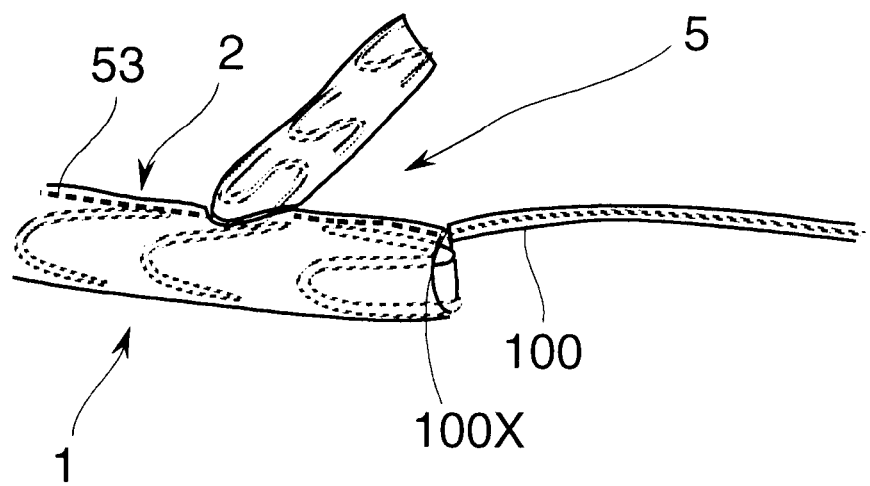
FIG. 22 is a view showing a preferable procedure to release the collapsing device.
Figure 23:
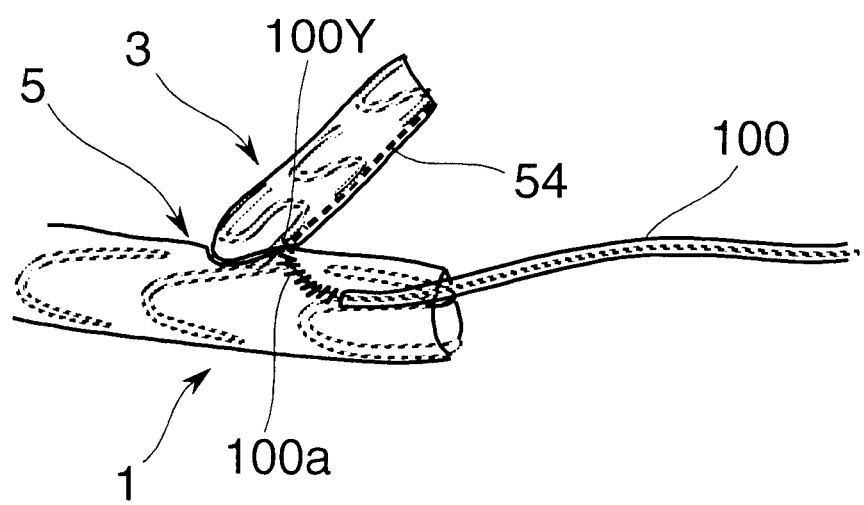
FIG. 23 is a view showing another preferable procedure to release the collapsing device.

Further, in case the wire 53 is drawn, if another tube 100 is fit over the wire 53 of the collapsing device 5 through a base side of the sheath, a tip 100X of the tube 100 is moved to a position where the artificial blood vessel 1 is to be implanted and the wire 53 is pulled with the tip 100X pushed against the rear of the artificial blood vessel 1, as shown in FIG. 22, it becomes possible to draw the wire 53 out of the body portion 3 without unnecessary force applied to the whole of the artificial blood vessel 1. More specifically, in order to draw out the wire 54 which keeps the branch portion 3 in a collapsed condition, if a flexible helical spring 100*a* is connected to a front tip of the tube 100, a front tip 100Y of the helical spring 100*a* is bent along the wire 54 which keeps the branch portion 3 in a collapsed condition and the front tip 100Y is placed at the base end of the branch portion 3, as shown in FIG. 23, a direction of pull to which the wire 54 is drawn is optimized, thereby to effectively avoid inconveniences such as a case that the wire 54 is broken.

Figure 24:
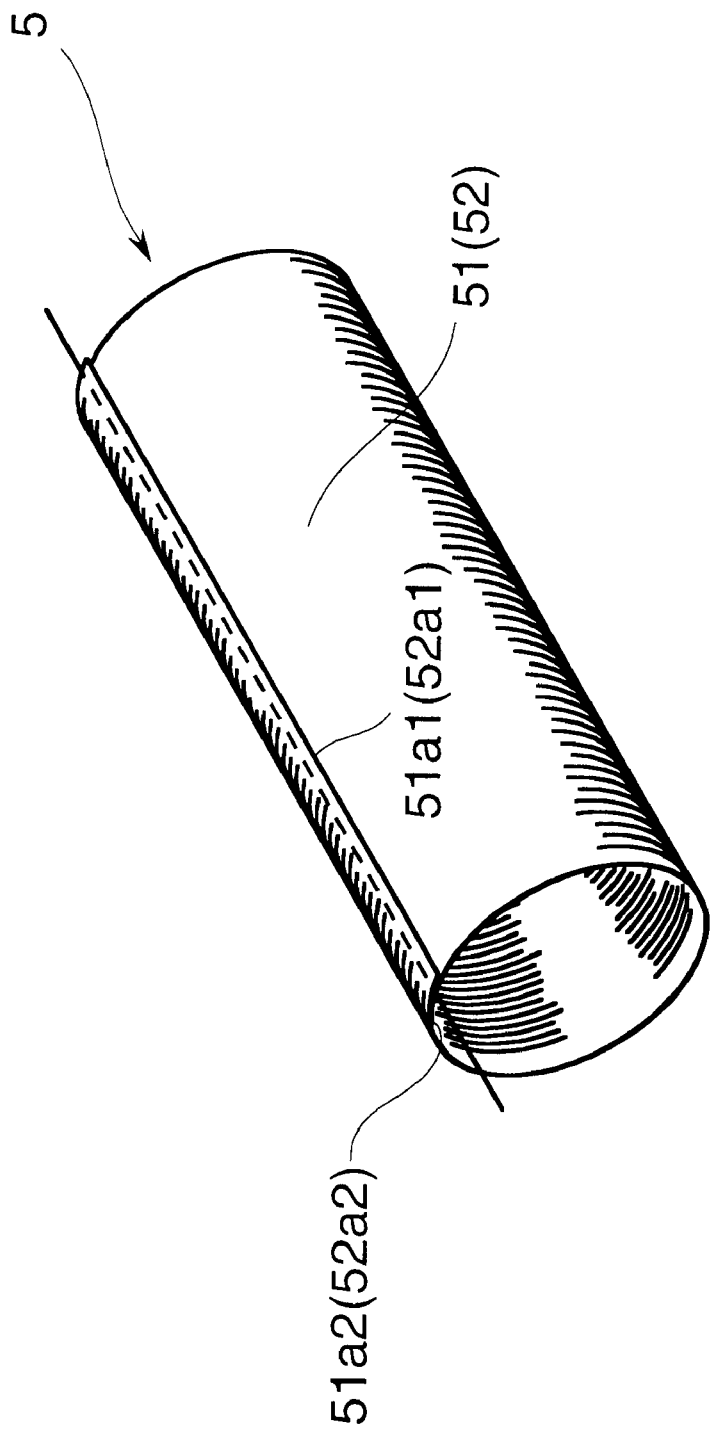
FIG. 24 is a perspective view showing another collapsing device of the invention.

In the above embodiment the collapsing device is so arranged that each edge of the wrapping member faces outward of a tube shape, however, it may be variously modified such as the wrapping member is rolled so as to be in a tube shape wherein one edge 51*a*1 (52*a*1) locates outside of the tube shape and the other edge 51*a*2 (52*a*2) locates inside of the tube shape as shown in FIG. 24.

In addition, the retaining member may be a string and so arranged that the string sews both edges of the wrapping member and a retaining rod such as a wire is passed through a loop portion formed at an end portion of the string. In this case it is possible to keep a shape of a tube. And it is also possible to release the wrapping member from a condition of being held indirectly if the retaining member is hauled so as to be separated from the loop, which will release the string from being restrained from moving. Especially, if the string is elastic, it is easy to release a condition of being kept.

POSSIBLE APPLICATIONS IN INDUSTRY

As mentioned above, the collapsing device for the appliance and the method of using the collapsing device in accordance with the invention make it possible to preferably wrap the appliance in a collapsed condition without bringing about an uneven portion on a surface thereof, to keep a condition in which the collapsing device can be transported to a target position by smoothly passing through a curved portion in a human body and to release the appliance from a collapsed condition with ease by a remote control, thereby to make it possible to preferably be utilized for implanting a various kinds of appliances such as an artificial blood vessel into a human body.

What is claimed is:

1. A collapsing device in combination with a collapsible/restorable elastic appliance, comprising:
a collapsing device having:
a first wrapping member which is generally flat when spread and a first retaining member which keeps the first wrapping member in a condition of being rolled and
a second wrapping member which is generally flat when spread and a second retaining member which keeps the second wrapping member in a condition of being rolled; and
a collapsible/restorable elastic appliance having a tubular body portion and a tubular branch portion which branches from a part of the tubular body portion, with the internal space of the branch portion communicating with the internal space of the tubular body portion, wherein
the appliance is arranged so that the body portion is contained in a collapsed condition inside the first wrapping member held in a rolled condition by the first retaining member and the branch portion is contained in a collapsed condition inside the second wrapping member held in a rolled condition by the second retaining member, and
the collapsing device keeps the appliance in a collapsed condition for transport to a target position and permits restoration of the appliance into a predetermined shape by releasing the appliance from the collapsed condition when the retaining members are separated from the wrapping members.

2. The collapsing device in combination with a collapsible/restorable elastic appliance as described in claim 1, wherein the body portion comprises intermittently arranged ring members bridged by a first flexible cover and the branch portion comprises intermittently arranged ring members bridged by a second flexible cover which branches from a part of the body portion, wherein the body portion and branch portion of the appliance are so arranged that each of the ring members is collapsed into a wavy shape having a peak and a valley.

3. A method of using a collapsing device in combination with a collapsible/restorable elastic appliance as described in claim 1, characterized by that the first wrapping member is mounted near an end portion of an outer circumference of a pipe member, the body portion and the branch portion of the appliance are inserted together into the pipe member at a position corresponding to the position where the first wrapping member is mounted and the first wrapping member and the body portion are drawn simultaneously out of the pipe member in a condition that both of the first wrapping member and the body portion are restrained from moving interactively at the end portion so as to contain the body portion and the branch portion of the appliance together inside of the first wrapping member, and subsequently a part of the first wrapping member is released from a condition of being held by the first retaining member and the branch portion is drawn out through the part of the first wrapping member and then the second wrapping member is mounted near an end portion of an outer circumference of a pipe member, the branch portion inserted into the pipe member and corresponding to the position where the second wrapping member is mounted and the second wrapping member and the branch portion are drawn simultaneously out of the pipe member in a condition that both of the second wrapping member and the branch portion are restrained from moving interactively so as to contain the branch portion inside of the second wrapping member.

4. The method of using the collapsing device in combination with a collapsible/restorable elastic appliance as described in claim 3, wherein the first wrapping member is made to open wider gradually along a tapered guide portion and then to be mounted on an outer circumference of the pipe member arranged at a position continuous to the guide portion.

5. A collapsing device in combination with a collapsible/restorable elastic appliance, comprising:

a collapsing device having:

a first wrapping member which is generally flat when spread and a first retaining member which keeps the first wrapping member in a condition of being rolled and a second wrapping member which is generally flat when spread and a second retaining member which keeps the second wrapping member in a condition of being rolled, wherein at least one of the first and second retaining members comprises a string which sews edges of a respective one of the first and second wrapping members and is arranged such that a retaining rod is passed through a loop formed at an end portion of the string; and a collapsible/restorable elastic appliance having a tubular body portion and a tubular branch portion which branches from a part of the tubular body portion, with the internal space of the branch portion communicating with the internal space of the tubular body portion, wherein the appliance is arranged so that the body portion is contained in a collapsed condition inside the first wrapping member held in a rolled condition by the first retaining member and the branch portion is contained in a collapsed condition inside the second wrapping member held in a rolled condition by the second retaining member, and the collapsing device keeps the appliance in a collapsed condition for transport to a target position and permits restoration of the appliance into a predetermined shape by releasing the appliance from the collapsed condition when the retaining members are separated from the wrapping members.

* * * * *